US007531640B2

(12) United States Patent
Lou et al.

(10) Patent No.: US 7,531,640 B2
(45) Date of Patent: May 12, 2009

(54) MONOCLONAL ANTIBODIES THAT RECOGNIZE A SHARED EPITOPE BETWEEN THE HUMAN IMMUNODEFICIENCY VIRUS TYPE 1 (HIV-1) CAPSID (CA/P24) AND THE HUMAN IMMUNODEFICIENCY VIRUS TYPE 2 (HIV-2) CAPSID (CA/P26)

(75) Inventors: Sheng C. Lou, Libertyville, IL (US); Jeffrey C. Hunt, Mundelein, IL (US); John G. Konrath, Lake Villa, IL (US); Xiaoxing Qiu, Gurnee, IL (US); James W. Scheffel, Mundelein, IL (US); Joan D. Tyner, Beach Park, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 36 days.

(21) Appl. No.: 10/940,262

(22) Filed: Sep. 14, 2004

(65) Prior Publication Data

US 2005/0053924 A1      Mar. 10, 2005

Related U.S. Application Data

(62) Division of application No. 09/731,126, filed on Dec. 6, 2000, now Pat. No. 6,818,392.

(51) Int. Cl.
*C12P 21/08* (2006.01)
(52) U.S. Cl. .................... 530/388.35; 422/61
(58) Field of Classification Search .............. 424/148.1, 424/208.1; 422/61
See application file for complete search history.

(56) References Cited

U.S. PATENT DOCUMENTS

| | | | |
|---|---|---|---|
| 4,886,742 | A | 12/1989 | Kortright et al. |
| 4,888,290 | A | 12/1989 | Kortright et al. |
| 5,173,399 | A | 12/1992 | Mehta et al. |
| 5,210,181 | A | 5/1993 | Butman et al. |
| 5,514,541 | A | 5/1996 | Butman et al. |
| 5,612,453 | A | 3/1997 | Wolf Hans et al. |
| 5,731,189 | A | 3/1998 | Zolla-Pazner et al. |
| 6,593,079 | B1 | 7/2003 | Donie et al. ............ 435/5 |

FOREIGN PATENT DOCUMENTS

| | | |
|---|---|---|
| DE | 19727943 | 9/1998 |
| EP | 034561 A | 12/1989 |
| EP | 0519866 A1 | 12/1992 |
| WO | 9014358 A | 11/1990 |
| WO | WO 93/21346 | 10/1993 |
| WO | 9840744 | 9/1998 |

OTHER PUBLICATIONS

Max, E. E., "Immunoglobulins: Molecular Genetics", in Fundamental Immunology, Fourth Edition, W. E. Paul, ed., Lippincott-Raven Publishers, Philadelphia, 1999, pp. 142-143.*
Allain, et al., *The Lancet*, Serological Markers in Early Stages of Human Immunodeficiency Virus Infection in Haemophiliacs, ii:1233-1236 (1986).
Barin, et al., *Science*, Virus Envelope Protein of HTLV-III Represents Major Target Antigen for Antibodies in AIDS Patients, 228:1094-1096 (1985).
Barin, et al., *The Lancet*, Serological Evidence for Virus Related to Simian T-Lymphotropic Retrovirus III in Residents of West Africa, 2:1387-1389 (1985).
Bowen, et al., *Annals of Internal Medicine*, Transmission of Human Immunodeficiency Virus (HIV) by Transplantation: Clinical Aspects and Time Course Analysis of Viral Antigenemia and Antibody Production, Ann. Of Int. Med. 108:46-48 (1988).
R.H. Burdon and P.H. van Knippenberg, eds. vol. 15 Elsevier, Amsterdam.
Charneau, et al., *Virology*, Isolation and Envelope Sequence of a Highly Divergent HIV-1 Isolate: Definition of a New HIV-1 Group, 205:247-253 (1994).
Clavel, et al., *Science*, Isolation of a New Human Retrovirus from West Africa Patients with AIDS, 233:343-346 (1986).
Clavel, et al., *Nature*, Molecular Cloning and Polymorphism of the Human Immune Deficiency Virus Type 2, 324:691-695 (1986).
Coffin, *Science*, HIV Population Dynamics in Vivo: Implications for Genetic Variation, Pathogenesis and Therapy, 267:483-489 (1995).
Courouce, et al., La Gazette de la Transfusion N°155-Mars-Avril (1999).
Dawson, et al., *The Journal of Infectious Diseases*, Reliable Detection of Individuals Seropositive for the Human Immunodeficiency Virus (HIV) by Competitive Immunoassays Using *Escherichia coli*-Expressed HIV Structural Proteins, 157:149-155 (1988).
Devare, et al., *Human Immunodeficiency Virus: Innovative Techniques, Monograph in Virology*, Diagnosis and Monitoring of HIV-1 and HIV-2 Infection, J.L. Melnick (ed.) Basel, Karger, vol. 18: 105-121 (1990).
Euler, et al., *Clinical and Experimental Immunology*, Precipitable Immune Complexes in Healthy Homosexual Men, Acquired Immune Deficiency Syndrome and the Related Lymphadenopathy Syndrome, 59:267-275 (1985).
Gao, F., et al., *Nature*, Origin of HIV-1 in the Chimpanzee Pan Troglodytes Troglodytes, 397:436-441 (1999).
Gonda, et al., *Science*, Sequence Homology and Morphologic Similarity of HTLV-III and Visna Virus, a Pathogenic Lentivirus, 277:177-179 (1985).
Goudsmit, et al., *The Lancet*, Expression of Human Immunodeficiency Virus Antigen (HIV-Ag) In Serum and Cerebrospinal Fluid During Acute and Chronic Infection, ii:177-180 (1986).
Griffith, et al., *Journal of Clinical Microbiology*, Stability of Free and Complexed Human Immunodeficiency Virus Type 1 and Antigen at 4° C. and at Room Temperature, 33:1348-1350 (1995).

(Continued)

*Primary Examiner*—Jeffrey S. Parkin
(74) *Attorney, Agent, or Firm*—Audrey L. Bartnicki; Cheryl L. Becker

(57) ABSTRACT

The present invention relates to novel monoclonal antibodies which may be used in the detection of Human Immunodeficiency Virus (HIV). These antibodies exhibit an unusually high degree of sensitivity, a remarkably broad range of specificity, and bind to novel shared, non-cross-reactive epitopes. In particular, the monoclonal antibodies of the present invention may be utilized to detect HIV-1 antigen and HIV-2 core antigen in a patient sample.

4 Claims, 14 Drawing Sheets

OTHER PUBLICATIONS

Gupta, et al., *New England Journal of Medicine*, Correspondence: Circulating Immune Complexes in AIDS, 310:1530-1531 (1984).

Gurtler, et al., *Journal of Virological Methods*, Reactivity of Five Anti-HIV-1 Subtype O Specimens with Six Different Anti-HIV Screening ELISAs and Three Immunoblots, 51:177-184 (1995).

Gurtler, et al., *Journal of Virological Methods*, Reduction of the Diagnostic Window with a New Combined p24 Antigen and Human Immunodeficiency Virus Antibody Screening Assay, 75:27-38 (1998).

Gurtler, et al., *Journal of Virological Methods*, A New Subtype of Human Immunodeficiency Virus Type 1 (MVP-5180) From Cameroon, 68:1581-1585 (1994).

Guyader, et al., *Nature*, Genome Organization and Transactivation of the Human Immunodeficiency Virus Type 2, 326:662-669 (1987).

Haesevelde, et al., *Journal of Virology*, Genomic Cloning and Complete Sequence Analysis of a Highly Divergent African Human Immunodeficiency Virus Isolate, 68:1586-1596 (1994).

Hunt, et al., *AIDS Research and Human Retroviruses*, Envelope Sequence Variability and Serologic Characterization of HIV Type 1 Group O Isolates from Equatorial Guinea, 13:995-1005 (1997).

Kageyama, et al., *Journal of Virological Methods*, An Improved Method for the Detection of HIV Antigen in the Blood of Carriers, 22:125-131 (1988).

Kanki, et al., *Science*, New Human T-Lymphotropic Retrovirus Related to Simian T-Lymphotropic Virus Type III (STLV-III$_{AGM}$), 232:238-243 (1986).

Kanki, et al., *Science*, Human T-Lymphotropic Virus Type 4 and the Human Immunodeficiency Virus in West Africa, 236:827-831 (1987).

Karush, F. *In Comprehensive Immunology*, ed. R.A. Good, S.B. Day, The Affinity of Antibody: Range, Variability and the Role of Multivalence, 5:85-116 (1978).

Kenny, et al., *The Lancet*, HIV Antigen Testing, 1(8532):565-566 (1987).

Kessler, et al., *JAMA*, Diagnosis of Human Immunodeficiency Virus Infection in Seronegative Homosexuals Presenting with an Acute Viral Syndrome, 258:1196-1199 (1987).

Ly, et al., *Journal of Clinical Microbiology*, Contributions of Combined Detection Assays of P-24 Antigen and Anti-Human Immunodeficiency Virus (HIV) Antibodies in Diagnosis of Primary HIV Infection by Routine Testing, 38(6): 2459-2461 (2000).

Mariuzza, et al., *Rev. Biophys. Chem.*, The Structural Basis of Antigen-Antibody Recognition, 16:139-159 (1987).

Mathiesen, et al., *Journal of Virological Methods*, Acid Hydrolysis of Serum Samples to Increased Detection of HIV Antigen, 22:143-148 (1988).

Mauclere, P. *AIDS*, Serological and Virological Characterization of HIV-1 Group O Infection in Cameroon, 11:445-453 (1997).

Mellors, et al., *Science* Prognosis in HIV-1 Infection Predicted by the Quantity of Virus in Plasma, 275:1167-1170 (1996).

Meyerhans, et al., *Cell*, Temporal Fluctuations in HIV Quasispecies in Vivo are not Reflected by Sequential HIV Isolations, 58:901-910 (1989).

Montagnier, et al., *Virology*, Identification and Antigenicity of the Major Envelope Glycoprotein of Lymphadenopathy-Associated Virus, 144:283-289 (1985).

Mulder, et al., *Journal of Clinical Microbiology*, Rapid and Simple PCR Assay for Quantitation of Human Immunodeficiency Virus Type 1 RNA in Plasma: Application to Acute Retroviral Infection, 32:292-300 (1994).

Phair, *JAMA*, Human Immunodeficiency Virus Antigenemia, 258:p. 1218 (1987).

Robertson, et al., *Nature*, Recombination of HIV-1, 374:124-126 (1995).

Saag, et al., *Nature Medicine*, HIV Viral Load Markers in Clinical Practice, 2:625-629 (1996).

Sarngadharan, et al., *Science*, Antibodies Reactive with Human T-Lymphotropic Retroviruses (HTLV-III) in the Serum of Patients with AIDS, 224:506-508 (1984).

Schochetman, et al., Aids Testing, Springer-Verlag, New York, Berlin, Heidelberg.

Schulz, et al., *The Lancet*, Envelope Gene-Derived Recombinant Peptide in the Serodiagnosis of Human Immunodeficiency Virus Infection, 2:111-112 (1986).

Schupbach, et al., *AIDS*, Heat-Mediated Immune Complex Dissociation and Enzyme-Linked Immunosorbent Assay Signal Amplification Render p24 Antigen Detection in Plasma as Sensitive as HIV-1 RNA Detection by Polymerase Chain Reaction, 10:1085-1090 (1996).

Sharp, et al., *Biological Bulletin*, Origins and Evolution of AIDS Viruses, 196:338-342 (1999).

Simmonds, et al., *Journal of Virology*, Human Immunodeficiency Virus-Infected Individuals Contain Provirus in Small Numbers of Peripheral Mononuclear Cells and a Low Copy Numbers, 64(2):864-872 (1990).

Steindl, et al., *Journal of Immunological Methods*, A Simple and Robust Method for the Complete Dissociation of HIV-1 p24 and Other Antigens from Immune Complexes in Serum and Plasma Samples, 217:143-151 (1998).

Stephens, et al., *Science*, Equine Infectious Anemia Virus gag and pol Genes: Relatedness to Visna and AIDS Virus, 231:589-594 (1986).

Stute, *The Lancet*, HIV Antigen In Acute HIV Infection, 1(8532): p. 566 (1987).

van Binsbergen, et al., *Journal of Virological Methods*, Improved Performance of Seroconversion with a 4$^{th}$ Generation HIV Antigen/Antibody Assay, 82:77-84 (1999).

Von Sydow, et al., *British Medical Journal*, Antigen Detection in Primary HIV Infection, 296:238-240 (1988).

Wain-Hobson, *Current Topics in Microbiology*, Human Immunodeficiency Virus Type 1 Quasispecies in Vivo and Ex Vivo, 176:181-193 (1992).

Wall, et al., *The Lancet*, HIV Antigenaemia in Acute HIV Infection, 1(8532):p. 566 (1987).

Weber, et al., *Journal of Clinical Microbiology*, Reduction of Diagnostic Window by New Fourth-Generation Human Immunodeficiency Virus Screening Assays, 36(8):2235-2239 (1998).

Zhang, et al., *AIDS*, Detection, Quantification and Sequencing of HIV-1 from the Plasma of Seropositive Individuals and from Factor VIII Concentrates, 5(6):675-681 (1991).

Zhu, *Journal of Virology*, Evidence for Coinfection by Multiple Strains of Human Immunodeficiency Virus Type 1 Subtype B in an Acute Seroconvertor, 69:1324-1327 (1995).

Niedrig, M. et al., *Journal of Virology*, Characterization of Murine Monoclonal Antibodies Directed Against the Core Proteins of Human Immunodeficiency Virus Types 1 and 2, 65/8:4529-4533 (1991).

Minassian, A.A, et al., *Monoclonal Antibodies Against Human Immunodeficiency Virus HIV Type 2 Core Proteins Cross-Reactivity With HIV Type 1 and Simian Immunodeficiency Virus*, 6/18:6939-6943 (1988).

Zolla-Pazner, Susan, et al., *Proceedings of the National Academy of Sciences of the United States*, "The Implication of Antigenic Diversity for Vaccine Development," Immunology Letters, 66/1-3: 159-164 (Mar. 1999).

* cited by examiner

```
                                 helix A              helix B
                                 ‾‾‾‾‾‾‾‾‾‾‾         ‾‾‾‾‾‾‾‾
HIV-1'O'    1   PVVPNAQGQMIHQALSPRTLNAWVKAVEEKAFNPEIIPMFMALSEGAIPY   50
                |:| | |||| :|||:||||||||||| ||||||| ||:|||| ||||||| |
HIV-1'M'    1   PIVQNIQGQMVHQAISPRTLNAWVKVVEEKAFSPEVIPMFSALSEGATPQ   50
                            M1/01 pept.
                |-----------------|M2.02pept.
                           |-----------------|  M3/03 pept
                                       |----------------- helix C            helix D
                     ‾‾‾‾‾‾‾           ‾‾‾‾‾‾‾‾‾‾‾‾‾‾‾‾‾‾
HIV-1'O'   51   DININMLNAIGGHQGALQVLKEVINEEAADWDRSHPPVVGPLPPGQIREPT  100
                |:|  ||| :|||| |:|.|||  ||||||:||| ||   ||:  |||.|||
HIV-1'M'   51   DLNTMLNTVGGHQAAMQMLKETINEEAAEWDRVHPVHAGP.IAPGQMREPR  100
                -------------|       M4/04 pept.
                        |---------------------| M5/05 pept.
                                   |--------------------
                                                |------ helix E   helix F    helix G
                 ‾‾‾‾‾‾‾   ‾‾‾‾‾‾‾   ‾‾‾‾‾‾‾‾
HIV-1'O'  101   GSDIAGTTSTQQEQVHWITRANHPVPVGDIYRKWIVLGLNKMVKMYSPVS  150
                ||||||||| |||: |.|  |  |:|||:|::||:|||||.|:|||| |
HIV-1'M'  101   GSDIAGTTSTLQEQIGWMTN.NPPIPVGEIYKRWIILGLNKIVRMYSPTS  149
                --|      M6/06 petp.
                ----------------------|
                          |-----------------|   M8/07 pept.
                                    |-----------------  ---------|
                                              |----------- helix H              helix I    helix J
                                ‾‾‾‾‾‾‾‾‾‾‾         ‾‾‾‾‾‾‾‾‾‾ ‾‾‾‾‾‾‾
HIV-1'O'  151   ILDIKQGPKEPFRDYVDRFYKTLRAEQAIQDVKNWMTETLLVQNANPDCK  200
                ||||:||||||||||||||||||||||||| |:|||||||||||||||||
HIV-1'M'  150   ILDIRQGPKEPFRDYVDRFYKTLRAEQASQEVKNWMTETLLVQNANPDCK  199
                     *****************  (MHR)
                       M9/09 pept.
                -------------------|
                       M10/010 pept.
                |---------------------| M11/011 pept.
                             |---------------------|

J        helix K
                                  ‾‾‾‾‾‾‾
HIV-1'O'  201   QILKALGPGATLEEMMVACQGVGGPTHKAKLL   232
                |||||||  |||||||| ||||||||| |||:.|
HIV-1'M'  200   TILKALGPAATLEEMMTACQGVGGPGHKARVL   231
                    M12/012 pept.
                ---------------|  M13/013 pept.
                           |------------|
```

FIG.1A

```
                         helix A              helix B
HIV-1'O'    1   PVVPNAQGQMTHQALSPRTLNAWVKAVEEKAFNPEIIPMFMALSEGAIPY   50
                |:| | ||||:|||:|||||||||| ||||||.||:|||| |||||| |
HIV-1'M'    1   PIVQNIQGQMVHQAISPRTLNAWVKVVEEKAFSPEVIPMFSALSEGATPQ   50
                | ||:  |: :|  :|||||||||||::||| |  ||:| |.||||| ||
HIV-2'A'    1   P.VQQAGGNYIHVPLSPRTLNAWVKLVEEKKFGAEVVPGFQALSEGCTPY   49 helix C        helix D
HIV-1'O'   51   DINIMLNAIGGHQGALQVLKEVINEEAADWDRSHPPVVGPLPPGQIREPT  100
                |:| ||| :|||| |:|.||| ||||||:|||  ||: |||·|||
HIV-1'M'   51   DLNTMLNTVGGHQAAMQMLKETINEEAAEWDRVHPVHAGPIAPGQMREPR  100
                |:| ||| || |||||||.::| ||||||:|| ||: ||: ||:|:||
HIV-2'A'   50   DINQMLNCVGDHQAAMQIIREIINEEAADWDAQHPIP.GPLPAGQLRDPR   98 helix E     helix F          helix G
HIV-1'O'  101   GSDIAGTTSTQQEQVHWITRANHPVPVGDIYRKWIVLGLNKMVKMYSPVS  150
                ||||||||||  |||: |.|   | |:||:||::||:|||||.|:|||| |
HIV-1'M'  101   GSDIAGTTSTLQEQIGWMTN.NPPIPVGEIYKRWIILGLNKIVRMYSPTS  149
                |||||||||| ||| ||      |:||| ||:||| :||:| ||||.||.
HIV-2'A'   99   GSDIAGTTSTVDEQIQWMYRQPNPVPVGNIYRRWIQIGLQKCVRMYNPTN  148 helix H           helix I      helix J
                 **************** (MHR)
HIV-1'O'  151   ILDIKQGPKEPFRDYVDRFYKTLRAEQAIQDVKNWMTETLLVQNANPDCK  200
                ||||:||||||||||||||||||||||| |:||||||||||||||||||
HIV-1'M'  150   ILDIRQGPKEPFRDYVDRFYKTLRAEQASQEVKNWMTETLLVQNANPDCK  199
                |||::||||| |. |||||||:|||||   ||||||||:|||:||||||
HIV-2'A'  149   ILDVKQGPKESFQSYVDRFYKSLRAEQTDPAVKNWMTQTLLIQNANPDCK  198

J     helix K
HIV-1'O'  201   QILKALGPGATLEEMMVACQGVGGPTHKAKLL  232
                |||||||| |||||||| ||||||| |||:.|
HIV-1'M'  200   TILKALGPAATLEEMMTACQGVGGPGHKARVL  231
                :|| ||    |||||:|||||||||  |||.|
HIV-2'A'  199   LVLKGLGMNPTLEEMLTACQGVGGPSQKARLM  230
```

FIG.1B

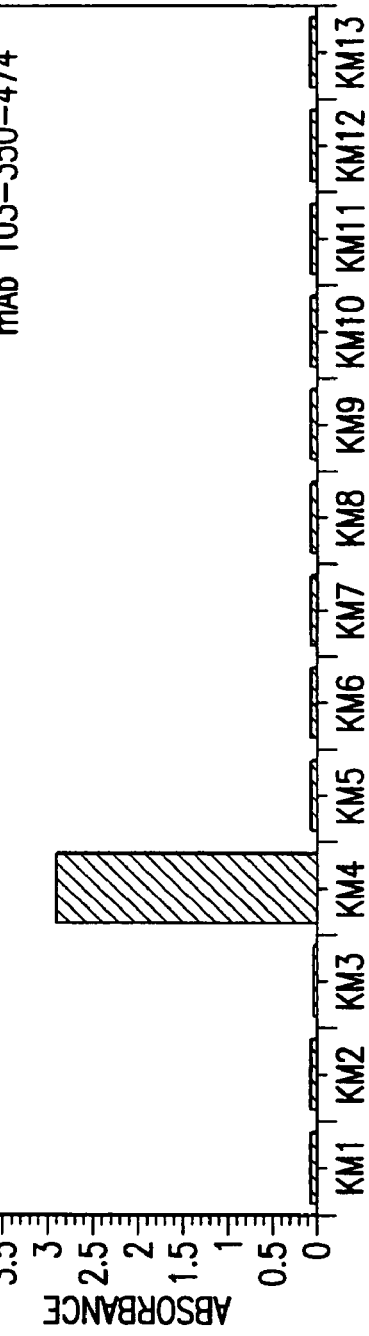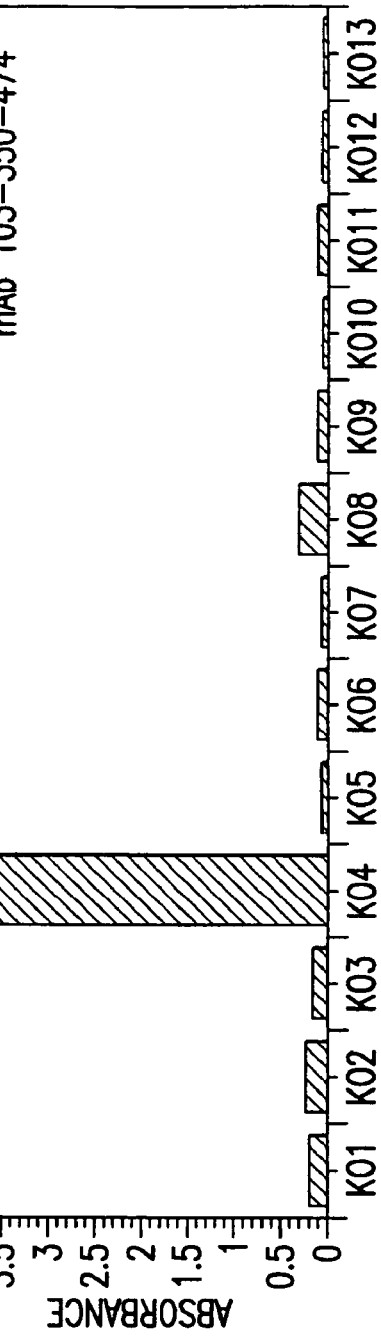

Western blot of mAb 115B-151-423 against deletion

HIV-1 'M' kDa
34
29
20
15

7

HIV-1 'O' kDa
34
29
20
15

7

| clones | C | E | F | G | H | I | L | M | N | O | P | Q |
|---|---|---|---|---|---|---|---|---|---|---|---|---|
| WB: | - | - | + | + | +/- | - | - | - | - | + | + | - | - |

Western blots of mAbs against p24 deletion clones

FIG. 4A

```
                         SEQUENCE LISTING

<160> NUMBER OF SEQ ID NOS: 9

<210> SEQ ID NO 1
<211> LENGTH: 28
<212> TYPE: PRT
<213> ORGANISM: Human Immunodeficiency Virus

<400> SEQUENCE: 1

Cys Gln Ala Ala Met Gln Met Leu Lys Glu Thr Ile Asn Glu Glu Ala
1               5                   10                  15

Ala Glu Trp Asp Arg Val His Pro Val His Ala Gly
            20                  25

<210> SEQ ID NO 2
<211> LENGTH: 28
<212> TYPE: PRT
<213> ORGANISM: Human Immunodeficiency Virus

<400> SEQUENCE: 2

Cys Gln Gly Ala Leu Gln Val Leu Lys Glu Val Ile Asn Glu Glu Ala
1               5                   10                  15

Ala Asp Trp Asp Arg Ser His Pro Pro Val Val Gly
            20                  25

<210> SEQ ID NO 3
<211> LENGTH: 27
<212> TYPE: PRT
<213> ORGANISM: Human Immunodeficiency Virus

<400> SEQUENCE: 3

Cys Leu Asp Ile Arg Gln Gly Pro Lys Glu Pro Phe Arg Asp Tyr Val
1               5                   10                  15

Asp Arg Phe Tyr Lys Thr Leu Arg Ala Glu Gln
            20                  25

<210> SEQ ID NO 4
<211> LENGTH: 27
<212> TYPE: PRT
<213> ORGANISM: Human Immunodeficiency Virus

<400> SEQUENCE: 4

Cys Leu Asp Ile Lys Gln Gly Pro Lys Glu Pro Pro Arg Asp Tyr Val
1               5                   10                  15

Asp Arg Phe Tyr Lys Thr Leu Arg Ala Glu Gln
            20                  25

<210> SEQ ID NO 5
```

```
<211> LENGTH: 20
<212> TYPE: PRT
<213> ORGANISM: Human Immunodeficiency Virus

<400> SEQUENCE: 5

Cys Lys Thr Ile Leu Lys Ala Leu Gly Pro Ala Ala Thr Leu Glu Glu
1               5                   10                  15

Met Met Thr Ala
            20

<210> SEQ ID NO 6
<211> LENGTH: 20
<212> TYPE: PRT
<213> ORGANISM: Human Immunodeficiency Virus

<400> SEQUENCE: 6

Cys Lys Gln Ile Leu Lys Ala Leu Gly Pro Gly Ala Thr Leu Glu Glu
1               5                   10                  15

Met Met Val Ala
            20

<210> SEQ ID NO 7
<211> LENGTH: 232
<212> TYPE: PRT
<213> ORGANISM: Human Immunodeficiency Virus

<400> SEQUENCE: 7

Pro Val Val Pro Asn Ala Gln Gly Gln Met Ile His Gln Ala Leu Ser
1               5                   10                  15

Pro Arg Thr Leu Asn Ala Trp Val Lys Ala Val Glu Glu Lys Ala Phe
            20                  25                  30

Asn Pro Glu Ile Ile Pro Met Phe Met Ala Leu Ser Glu Gly Ala Ile
        35                  40                  45

Pro Tyr Asp Ile Asn Ile Met Leu Asn Ala Ile Gly Gly His Gln Gly
    50                  55                  60

Ala Leu Gln Val Leu Lys Glu Val Ile Asn Glu Glu Ala Ala Asp Trp
65                  70                  75                  80

Asp Arg Ser His Pro Pro Val Val Gly Pro Leu Pro Gly Gln Ile
                85                  90                  95

Arg Glu Pro Thr Gly Ser Asp Ile Ala Gly Thr Thr Ser Thr Gln Gln
            100                 105                 110

Glu Gln Val His Trp Ile Thr Arg Ala Asn His Pro Val Pro Val Gly
        115                 120                 125

Asp Ile Tyr Arg Lys Trp Ile Val Leu Gly Leu Asn Lys Met Val Lys
    130                 135                 140

Met Tyr Ser Pro Val Ser Ile Leu Asp Ile Lys Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ile Gln Asp Val Lys Asn Trp Met Thr Glu Thr Leu Leu Val
            180                 185                 190

Gln Asn Ala Asn Pro Asp Cys Lys Gln Ile Leu Lys Ala Leu Gly Pro
        195                 200                 205

Gly Ala Thr Leu Glu Glu Met Met Val Ala Cys Gln Gly Val Gly Gly
    210                 215                 220

Pro Thr His Lys Ala Lys Leu Leu
225                 230
```

```
<210> SEQ ID NO 8
<211> LENGTH: 231
<212> TYPE: PRT
<213> ORGANISM: Human Immunodeficiency Virus

<400> SEQUENCE: 8

Pro Ile Val Gln Asn Ile Gln Gly Gln Met Val His Gln Ala Ile Ser
 1               5                  10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230

<210> SEQ ID NO 9
<211> LENGTH: 229
<212> TYPE: PRT
<213> ORGANISM: Human Immunodeficiency Virus

<400> SEQUENCE: 9

Val Gln Gln Ala Gly Gly Asn Tyr Ile His Val Pro Leu Ser Pro Arg
 1               5                  10                  15

Thr Leu Asn Ala Trp Val Lys Leu Val Glu Glu Lys Lys Phe Gly Ala
            20                  25                  30

Glu Val Val Pro Gly Phe Gln Ala Leu Ser Glu Gly Cys Thr Pro Tyr
        35                  40                  45

Asp Ile Asn Gln Met Leu Asn Cys Val Gly Asp His Gln Ala Ala Met
    50                  55                  60

Gln Ile Ile Arg Glu Ile Ile Asn Glu Glu Ala Asp Trp Asp Ala
65                  70                  75                  80

Gln His Pro Ile Pro Gly Pro Leu Pro Ala Gly Gln Leu Arg Asp Pro
                85                  90                  95
```

-continued

```
Arg Gly Ser Asp Ile Ala Gly Thr Thr Ser Thr Val Asp Glu Gln Ile
            100                 105                 110

Gln Trp Met Tyr Arg Gln Pro Asn Pro Val Pro Val Gly Asn Ile Tyr
        115                 120                 125

Arg Arg Trp Ile Gln Ile Gly Leu Gln Lys Cys Val Arg Met Tyr Asn
        130                 135                 140

Pro Thr Asn Ile Leu Asp Val Lys Gln Gly Pro Lys Glu Ser Phe Gln
145                 150                 155                 160

Ser Tyr Val Asp Arg Phe Tyr Lys Ser Leu Arg Ala Glu Gln Thr Asp
                165                 170                 175

Pro Ala Val Lys Asn Trp Met Thr Gln Thr Leu Leu Ile Gln Asn Ala
            180                 185                 190

Asn Pro Asp Cys Lys Leu Val Leu Lys Gly Leu Gly Met Asn Pro Thr
        195                 200                 205

Leu Glu Glu Met Leu Thr Ala Cys Gln Gly Val Gly Gly Pro Ser Gln
    210                 215                 220

Lys Ala Arg Leu Met
225
```

MONOCLONAL ANTIBODIES THAT RECOGNIZE A SHARED EPITOPE BETWEEN THE HUMAN IMMUNODEFICIENCY VIRUS TYPE 1 (HIV-1) CAPSID (CA/P24) AND THE HUMAN IMMUNODEFICIENCY VIRUS TYPE 2 (HIV-2) CAPSID (CA/P26)

The present application is a divisional of U.S. patent application Ser. No. 09/731,126, filed Dec. 6, 2000, now U.S. Pat. No. 6,818,392, hereby incorporated in its entirety by reference.

BACKGROUND OF THE INVENTION

1. Technical Field

The present invention relates to novel monoclonal antibodies which may be used in the detection of Human Immunodeficiency Virus (HIV). These antibodies exhibit an unusually high degree of sensitivity, a remarkably broad range of specificity, and bind to novel shared, non-cross-reactive epitopes. In particular, the monoclonal antibodies of the present invention may be utilized to detect HIV-1 antigen and HIV-2 core antigen in a patient sample.

2. Background Information

Acquired Immunodeficiency Syndrome (AIDS) is an infectious and incurable disease transmitted through sexual contact from HIV infected individuals or by exposure to HIV contaminated blood or blood products. HIV-1 includes the formerly named viruses Human T-cell Lymphotrophic Virus Type III (HTLV III), Lymphadenopathy Associated Virus (LAV), and AIDS Associated Retrovirus (ARV). HIV is a retrovirus related to a group of cytopathic retroviruses, namely lentiviruses, on the basis of morphologic features, genomic organization, and nucleotide sequence (Gonda et al., Science (1985) 277:177-179; Stephan et al., Science (1986) 231:589-594; Korber, B. (ed.) et al., Human Retroviruses and AIDS. A Compilation and Analysis of Nucleic Acid and Amino Acid Sequences. Published by Theoretical Biology and Biophysics, Los Alamos National Laboratory, Los Alamos, N. Mex.; Reviewed in, Schochetman, G. and George, J. R., (1994) AIDS Testing. Springer-Verlag, N.Y., Berlin, Heidelberg). HIV is an enveloped virus containing several structural proteins. Of particular relevance, the core of the virus is formed by condensation of cleavage products from a highly processed gag-pol polyprotein precursor (Pr180gag-pol) which is cleaved into a pol precursor and a gag precursor (Pr55gag). Subsequently, the core precursor Pr55gag is cleaved into p17 (myristilated gag protein), p24 (major structural protein), p7 (nucleic acid binding protein), and p9 (proline-rich protein). The envelope contains two structural proteins, gp120 (envelope glycoprotein) and gp41 (transmembrane protein) which are cleavage products of the envelope polyprotein precursor, gp160.

The most common markers of HIV infection are antibodies against viral structural proteins (Dawson, et.al., J. Infect. Dis.(1988) 157:149-155; Montagnier, et al. Virology (1985) 144:283-289; Barin, et al., Science (1985) 228:1094-1096; Schulz, T. F., et al., Lancet (1986) 2:111-112; Sarngadharan, et al., Science (1984) 224:506-508; Allan, et al., Science (1985) 228:1091-1093) and viremia in the form of detectable viral core antigen (antigenemia) (Kessler, et. al., JAMA (1987) 258:1196-1199; Phair, JAMA (1987) 258:p1218; Allain, et al., The Lancet (1986) ii:1233-1236; Kenny, et al., The Lancet (1987) 1 (8532):565-566; Wall, et al., The Lancet (1987) 1(8532):p566; Stute, The Lancet (1987) 1(8532):p566; Goudsmit, et al., The Lancet (1986) ii: 177-180; vonSydow, et al., Brit. Med. J. (1988) 296:238-240; Bowen, et al. Ann. of Int. Med. (1988) 108:46-48) or detectable viral nucleic acid (Mellors, et al., Science (1996) 272: 1167-1170; Saag, et al. Nat. Med. (1996) 2: 625-629; Mulder, et al. J. Clin. Microbiol. (1994) 32:292-300; Zhang, et al., AIDS (1991) 5(6):675-681; Simmonds, et al., J. Virology (1990) 64(2):864-872). For example, in the United States, screening of blood and blood products by tests to detect antibody or antigen is mandated (Federal Food, Drug, and Cosmetic Act, 21 U.S.C. \\(301 et. seq., Public Health Service Act 42 U.S.C. \\(201 et. seq.). Nucleic acid testing recently has been implemented in order to attain maximal reduction of the HIV seroconversion window (www.fda.gov). As a further example, various countries in Europe have begun to evaluate and use tests that detect antibody and antigen simultaneously (Ly, et al. J. Clin. Microbiol. (2000) 38(6): 2459-2461; Gurtler, et al., J. Virol. Methods (1998) 75: 27-38; Weber, et al., J. Clin. Microbiol (1998) 36(8): 2235-2239; Courouce', et al., La Gazette de la Transfusion (1999) N°155-Mars-Avril; Van Binsbergen, et al., J. Virol. Methods (1999) 82: 77-84), in addition to European implementation of nucleic acid testing. Serologic assays that combine antibody and antigen detection exhibit superior seroconversion sensitivity compared to assays that detect only antibody, because detection of antigen, which appears prior to antibody, reduces the seroconversion window. An early version of an HIV combo assay is described in Gallarda, et al., 1992, WO93/21346, Assay for Detection of HIV Antigen and Antibody.

Within several weeks after infection with HIV, individuals generally enter a clinical phase characterized by extensive viremia and acute symptoms. During this period, prior to seroconversion, HIV p24 core antigen can be detected transiently in serum or plasma specimens (antigenemia) (Devare, et al., (1990) In, Human Immunodeficiency Virus: Innovative Techniques. Monograph in Virology, J. L. Melnick (ed.), Basel, Karger, vol 18: 105-121; Kessler, et al. JAMA (1987 258: 1196-1199; Phair, J. P., JAMA (1987) 258: p1218; Allain, et al. The Lancet (1986) ii: 1233-1236; Kenny, et al., The Lancet (1987) 1(8532): 565-566; Wall, et al., The Lancet (1987) 1(8532): 566; Stute, R., The Lancet (1987) 1(8532): 566; Goudsmit, et al., The Lancet (1986) ii: 177-180; vonSydow, et al., Brit. Med. J. (1988) 296: 238-240; Bowen, et al., Ann. of Int. Med. (1988) 108: 46-48). After seroconversion, the core protein apparently is bound up by antibodies in circulating immune complexes, making core protein detection difficult and requiring immune complex disruption techniques (Schupbach, et al., AIDS (1996) 10:1085-1090; Kageyama, et al., J. Virol. Methods (1988) 22: 125-131; Mathiesen, et al., J. Virol. Methods (1988) 22: 143-148; Steindl, et al., J. Immunol. Methods (1998) 217: 143-151; Euler, et al., Clin. Exp. Immunol. (1985) 59: 267-275; Gupta, et al., New Eng. J. Med. (1984) 310: 1530-1531; Griffith, et al., J. Clin. Microbiol. (1995) 33: 1348-1350). After the initial viremic phase and throughout the remainder of the disease, the virus generally establishes a steady state level (reviewed in Coffin, J. M. Science (1995) 267: 483-489).

Core proteins from isolates of HIV-1 group O, HIV-1 group M, and HIV-2 are antigenically similar because they share regions of amino acid sequence homology. Human (or mouse) immune polyclonal sera (i.e., immunoglobulin) elicited against the core protein of one group or type will cross react against the core protein of a different group or type (Clavel, et al., Science (1986) 233; 343-346; Guyader, et al., Nature (1987) 326: 662-669; Barin, et al., Lancet (1985) 2: 1387-1389; Kanki, et al., Science (1986) 232: 238-243; Kanki, et al., Science (1987) 236: 827-831; Clavel, et al., Nature (1986) 324: 691-695; Hunt, et al., AIDS Res. Human Retroviruses (1997) 13: 995-1005; Gurtler, et al., J. Virol. Methods (1995) 51: 177-184; Mauclere, P. AIDS (1997) 11: 445-453). However, in contrast to human (or mouse) immune polyclonal sera, mouse or human monoclonal antibodies raised or elicited against the core protein of one HIV group or type may (Mehta, et al., U.S. Pat. No. 5,173,399; Butman, et al., U.S. Pat. No. 5,210,181; Butman, et al., U.S. Pat. No. 5,514,541) or may not (Mehta, et al., U.S. Pat. No. 5,173,399; Butman, et al., U.S. Pat. No. 5,210,181; Butman, et al., U.S. Pat. No. 5,514,541) react against the core protein of a different HIV group or type. Often, however, neither cross-reactivity nor shared reactivity (Tijssen, 1993 In, Laboratory Techniques in Biochemistry and Molecular Biology. R. H. Burdon and P. H. van Knippenberg, eds. Vol. 15. Elsevier, Amsterdam) of mouse monoclonal antibodies have been considered or taught (Kortright, et al., U.S. Pat. No. 4,888,290; Kortright, et al., U.S. Pat. No. 4,886,742). In cases where HIV-1 and HIV-2 core proteins were detected simultaneously (Butman, et al., U.S. Pat. No. 5,210,181; Butman, et al., U.S. Pat. No. 5,514,541), a combination of at least 3 monoclonals were required, and the resulting quantitative sensitivity against HIV-1 core protein was much greater (50-fold) than for HIV-2 core protein, indicating that the monoclonals identified cross-reactive epitopes and not shared epitopes. Typically, monoclonal antibodies display a lower affinity against cross-reactive antigens (epitopes) (Karush, F. (1978) In, Comprehensive Immunology, ed. R. A. Good, S. B. Day, 5: 85-116. New York/London: Plenum; Mariuzza, et al., Rev. Biophys. Biophys. Chem. (1987) 16: 139-159; Tijssen, (1993) In, Laboratory Techniques in Biochemistry and Molecular Biology. R. H. Burdon and P. H. van Knippenberg, eds. Vol. 15. Elsevier, Amsterdam) compared to the affinity against the immunizing antigen (epitope) or shared epitope, resulting in less sensitivity toward the cross-reactive antigen.

Shared epitopes are not readily identified, particularly within proteins of related but different sequence. A single amino acid change within an epitope can destroy or modify binding of a monoclonal antibody to that epitope (Mariuzza, et al., Rev. Biophys. Biophys. Chem. (1987) 16: 139-159). In addition, within proteins, amino acid changes (or differences) in sites outside of the epitope can change the epitope due to changes in protein folding (Mariuzza, et al., Rev. Biophys. Biophys. Chem. (1987) 16: 139-159; Laver, et al., Cell (1990) 61: 553-556), thus altering the binding of an antibody to the epitope. In this regard, the core proteins of HIV-1 Group M, HIV-1 Group O, and HIV-2 are related but not identical (Korber, ibid), and although it is known that cross-reactive epitopes exist between HIV core proteins, it is neither certain nor taught that shared epitopes are present.

The extensive genetic (and therefore antigenic) variability of HIV has not been predicted, although many scientific papers have sought to supply explanations for the mechanism(s) of variability (Meyerhans, et al., Cell (1989) 58: 901-910; Wain-Hobson, Curr. Top. Microbiol. Immunol. (1992) 176:181-193; Holland, et al., Curr. Top. Micorbiol. Immunol. (1992) 176: 1-20; Gao, F. et al., Nature (1999) 397: 436-441; Sharp, et al., Biol. Bull. (1999) 196: 338-342; Robertson, et al., Nature (1995) 374: 124-126; Zhu, J. Virol. (1995) 69: 1324-1327). Determination of HIV genetic (and therefore antigenic) variability has relied solely on many empirical observations that subsequently have led to phylogenetic classification based on variation of HIV nucleic and amino acid sequence (Korber, ibid). Similarly, prediction of shared epitopes between HIV (core) proteins cannot be made because (a) core protein sequences must first be discovered, (b) once discovered, genetic variation provides added complexity and uncertainty to the identification of shared epitopes and (c) epitope discovery and characterization are required to differentiate cross-reactive from shared epitopes. Shared epitopes between HIV-1 Group M, HIV-1 Group O, and HIV-2 could not be determined until the discovery of HIV-1 Group O in 1994 (Gurtler, et al., J. Virol. (1994) 68: 1581-1585; Haesevelde, et al., J. Virol. (1994) 68: 1586-1596; Charneau, et al., Virology (1994) 205: 247-253).

The role of monoclonal antibody affinity for equivalent quantitative detection of variable HIV core proteins generally has not been taught (Mehta, et al., U.S. Pat. No. 5,173,399; Gallarda, et al. WO93/21346; Zolla-Pazner, et al., U.S. Pat. No. 5,731,189; Mestan, et al., EP 0519866A1; Butman, et al., U.S. Pat. No. 5,210,181; Butman, et al., U.S. Pat. No. 5,514, 541; Kortright, et al., U.S. Pat. No. 4,888,290; Kortright, et al., U.S. Pat. No. 4,886,742). An average affinity for a monoclonal antibody elicited against a protein antigen is $4.5 \times 10^7$ $mol^{-1}$ (Mariuzza, et al., Rev. Biophys. Biophys. Chem. (1987) 16: 139-159; Karush, F. (1978) In, Comprehensive Immunology, ed. R. A. Good, S. B. Day, 5: 85-116. New York/London: Plenum). Additionally, immunization strategies to increase the probability of obtaining monoclonals against shared epitopes have not been taught.

Only by combining two unpredictable features of monoclonal antibodies, affinity and shared reactivity, can one reasonably expect to obtain monoclonal antibodies which can be used to detect equivalent amounts of related but non identical HIV core proteins. Simple cross-reactivity of monoclonal antibodies is likely to be insufficient to achieve equivalent quantitative detection of HIV core proteins. Rather, shared reactivity in combination with high affinity is required to achieve the desired result. The affinity of a monoclonal for a related core protein may be substantially lower than that determined with the immunizing core protein. In that case, the epitope is most likely cross-reactive and the affinity of the antibody for the cross-reactive epitope may severely limit the utility of the antibody for detection of diagnostically relevant (i.e., 25 pg p24/ml serum or plasma, Courouc•, et al., La Gazette de la Transfusion (1999) N° 155-Mars-Avril) concentrations of the cross reactive core protein.

There are currently no known descriptions of immunoassays using only 2 monoclonal antibodies to achieve equivalent quantitative detection of HIV-1 Group M, HIV-1 Group O, and HIV-2 core proteins. Thus, such an immunoassay is certainly desirable. Two or more monoclonals in combination with polyclonal sera (immunoglobulin) have provided the basis for immunoassays to detect HIV-1 core protein or simultaneously HIV-1 and HIV-2 core proteins (Mehta, et al., U.S. Pat. No. 5,173,399; Butman, et al., U.S. Pat. No. 5,210, 181; Butman, et al., U.S. Pat. No. 5,514,541; Kortright, et al., U.S. Pat. No. 4,888,290; Kortright, et al., U.S. Pat. No. 4,886, 742; Gallarda, et al. WO93/21346). Thus, in view of the above, previous literature fails to (a) describe or teach immunoassay restricted to two monoclonals for equivalent quantitative detection of HIV-1 Group M and HIV-2 core proteins, (b) describe or teach immunoassays restricted to two monoclonal antibodies for equivalent quantitative detections of HIV-1 group M, HIV-1 group O, and HIV-2 core proteins, (c) teach methods to overcome monoclonal affinity barriers recognizing cross-reactive antigens leading to non-equivalent detection of HIV-1 group M, O, and HIV core proteins, and (d) high affinity monoclonal antibodies against shared-epitopes as the methods and means to detect diagnostically relevant and equivalent amounts of non-identical core proteins from HIV-1 group M, HIV-2 group O, and HIV-2.

All U.S. patents, patent applications and publications referred to herein are hereby incorporated in their entirety by reference.

SUMMARY OF THE INVENTION

The present invention relates to monoclonal antibodies and methods of using these antibodies in the detection of Human Immunodeficiency Virus Type 1 (Groups M and O) and Type 2, the etiologic agents of Acquired Immunodeficiency Syndrome (AIDS), in serum, plasma, or other bodily fluids. In particular, the invention encompasses diagnostic methods that employ compatible, high affinity, unique mouse monoclonal antibodies identifying non-cross-reactive, shared epitopes in order to detect equivalent amounts of HIV-1 core protein (p24) and HIV-2 core protein (p26). Such antibodies also may be used in assays which detect HIV antigen and in combination assays that simultaneously detect HIV antigen and HIV antibody. In a preferred embodiment of the present invention, only two complementary, high affinity, broadly specific mouse monoclonal antibodies are required to detect equivalent amounts of core proteins from HIV-1 Group M, HIV-1 Group O, and HIV-2.

The monoclonal antibodies of the present invention have high affinities (Keq values) sufficient to detect diagnostically relevant femtomolar quantities of HIV core protein; however, they also possess broad specificity (i.e., shared-reactivity) for detection of equivalent quantities of related, but nonidentical, core proteins from HIV-1 Group M, HIV-1 Group O, and HIV-2.

In particular, the present invention encompasses monoclonal antibodies which specifically bind to Human Immunodeficiency Virus-1 groups O and M protein p24 and Human Immunodeficiency Virus-2 protein p26. These monoclonal antibodies are, for example, 120A-270, 115B-151, 103-350, 115B-303, 117-289, and 108-394. The present invention also includes the hybridomas that produce these antibodies.

Furthermore, the present invention also encompasses a method for detecting the presence of one or more antigens selected from the group consisting of HIV-1 antigen and HIV-2 antigen, in a test sample suspected of containing one or more of the antigens. The method comprises the steps of: a) contacting the test sample with at least one monoclonal antibody (e.g., 120A-270) which specifically binds to shared epitopes on Human Immunodeficiency Virus-1 protein p24 and Human Immunodeficiency Virus-2 protein p26 for a time and under conditions sufficient for the formation of antibody/antigen complexes; and b) detecting the complexes, presence of the complexes indicating presence of at least one antigen selected from the group consisting of HIV-1 antigen and HIV-2 antigen, in the test sample. The monoclonal of step (a) may be, for example, any one of the monoclonal antibodies described herein. It may or may not be labeled. Preferably, only one monoclonal antibody is contacted with the test sample.

The present invention also includes a method for simultaneously detecting the presence of one or more antigens selected from the group consisting of HIV-1 antigen and HIV-2 antigen, in a test sample suspected of containing one or more of the antigens. The method comprises the steps of: a) contacting the test sample with at least one monoclonal antibody which specifically binds to Human Immunodeficiency Virus-1 protein 24 and Human Immunodeficiency Virus-2 protein p26 for a time and under conditions sufficient for the formation of antibody/antigen complexes; b) adding a conjugate to the resulting antibody/antigen complexes for a time and under conditions sufficient to allow the conjugate to bind to the bound antigen, wherein the conjugate comprises an antibody attached to a signal generating compound capable of generating a detectable signal; and c) detecting the presence of antigen which may be present in the test sample by detecting a signal generated by the signal-generating compound, presence of the signal indicating presence of at least one antigen selected from the group consisting of HIV-1 antigen and HIV-2 antigen in the test sample. The at least one monoclonal antibody of step (a) may be, for example, 120A-270, 115B-151, 117-289, 103-350, 108-394 or 115B-303. Preferably, one monoclonal antibody is used, in particular, 120A-270. The antibody of step (b) of the conjugate may be, for example, 120A-270, 115B-151, 117-289, 103-350, 108-394 or 115B-303, and is preferably 115B-151. Preferably, monoclonal antibody 120A-270 (or 117-289) and monoclonal antibody 115B-151 are used as a pair, whether 120A-270 (or 117-289) is on the solid phase or is present in the conjugate, or whether 115B-151 is on the solid phase or is present in the conjugate.

Moreover, the present invention also encompasses a method for detecting the presence of one or more antigens selected from the group consisting of HIV-1 antigen and HIV-2 antigen, in a test sample suspected of containing one or more of these antigens, comprising the steps of: (a) simultaneously contacting: 1) at least one monoclonal antibody, which specifically binds to HIV-1 p24 antigen and HIV-2 p26 antigen, bound to a solid support, 2) the test sample, and 3) an indicator reagent comprising an antibody which specifically binds to HIV-1 antigen and HIV-2 antigen to which a signal generating compound is attached, to form a mixture; (b) incubating the mixture for a time and under conditions sufficient to form antibody/antigen/antibody complexes; (c) detecting the presence of a measurable signal generated by the signal-generating compound, presence of the signal indicating presence of one or more antigens in said test sample selected from the group consisting of HIV-1 antigen and HIV-2 antigen. The at least one monoclonal antibody of step (a) may be, for example, 120A-270, 115B-151, 117-289, 108-394, 115B-303 or 103-350, and is preferably 120A-270. The antibody of the conjugate of step (b) may be, for example, 120A-270, 115B-151, 117-289, 108-394, 115B-303 or 103-350, and is preferably 115B-151. Again, it is important to note that any one or more monoclonal antibodies of the present invention may be used on the solid phase in connection with any other monoclonal antibody of the invention (in the conjugate or solution phase). Certain pairs of monoclonal antibodies are preferred, however, and it is preferable to have only one monoclonal antibody on the solid phase.

The present invention also includes a kit for determining the presence of one or more antigens selected from the group consisting of HIV-1 antigen and HIV-2 antigen in a test sample comprising: (a) at least one monoclonal antibody which which specifically binds to Human Immunodeficiency Virus-1 protein p24 and Human Immunodeficiency Virus-2 protein p26; and (b) a conjugate comprising an antibody attached to a signal-generating compound capable of generating a detectable signal. The at least one monoclonal antibody of (a) may be, for example, 120A-270, 115B-151, 117-289, 108-394, 115B-303, or 103-350, and is preferably 120A-270. The antibody of (b) may be, for example, 120A-270, 115B-151, 117-289, 108-394, 115B-303, or 103-350, and is preferably 115B-151.

The present invention also includes a diagnostic reagent comprising at least one monoclonal antibody selected from the group consisting of 120A-270, 115B-151, 117-289, 103-350, 108-394 and 115B-303.

Additionally, the present invention encompasses isolated epitopes or peptides having the amino acid sequences shown in SEQ ID Nos: 1-6.

The present invention also includes methods of simultaneously detecting both antigen and antibody to HIV-1 and/or HIV-2 in a patient sample. One such method involves detecting 1) one or more antibodies selected from the group consisting of HIV-1 antibody and HIV-2 antibody, and 2) one or more antigens selected from the group consisting of HIV-1 antigen and HIV-2 antigen, in a test sample suspected of containing one or more of the antibodies and one or more of said antigens, comprising the steps of: a) contacting the test sample with at least one HIV-1 antigen which binds to HIV-1 antibody for a time and under conditions sufficient for the formation of HIV-1 antigen/HIV-1 antibody complexes; b) detecting the HIV-1 antigen/HIV-1 antibody complexes, presence of the complexes indicating presence of HIV-1 antibody in the test sample; c) contacting the test sample with at least one HIV-2 antigen which binds to HIV-2 antibody for a time and under conditions sufficient for the formation of HIV-2 antigen/HIV-2 antibody complexes; d) detecting the HIV-2 antigen/HIV-2 antibody complexes, presence of the complexes indicating presence of HIV-2 antibody in the test sample; e) contacting the test sample with at least one monoclonal antibody which specifically binds to Human Immunodeficiency Virus-1 protein p24 and Human Immunodeficiency Virus-2 protein p26 for a time and under conditions sufficient for the formation of antibody/antigen complexes; and f) detecting the complexes, presence of the complexes indicating presence of at least one antigen selected from the group consisting of HIV-1 antigen and HIV-2 antigen, in the test sample. Again, it is preferable to utilize certain pairs of monoclonal antibodies in connection with HIV-1 and HIV-2 antigen detection (e.g., 120A-270 and 115B-151).

Another method enocompassed by the present invention involves detecting 1) one or more antibodies selected from the group consisting of HIV-1 antibody and HIV-2 antibody, and 2) one or more antigens selected from the group consisting of HIV-1 antigen and HIV-2 antigen, in a test sample suspected of containing one or more of the antibodies and one or more of the antigens, comprising the steps of: a) contacting the test sample with at least one HIV-1 antigen which specifically binds to HIV-1 antibody for a time and under conditions sufficient for the formation of HIV-1 antigen/HIV-1 antibody complexes; b) adding a conjugate to the resulting HIV-1 antigen/HIV-1 antibody complexes for a time and under conditions sufficient to allow the conjugate to bind to the bound antibody, wherein the conjugate comprises an antigen attached to a signal-generating compound capable of generating a detectable signal; c) detecting HIV-1 antibody which may be present in the test sample by detecting a signal generated by the signal-generating compound, presence of the signal indicating presence of HIV-1 antibody in the test sample; d) contacting the test sample with at least one HIV-2 antigen which specifically binds to HIV-2 antibody for a time and under conditions sufficient for the formation of HIV-2 antigen/HIV-2 antibody complexes; e) adding a conjugate to the resulting HIV-2 antigen/HIV-2 antibody complexes for a time and under conditions sufficient to allow the conjugate to bind to the bound antibody, wherein the conjugate comprises an antigen attached to a signal generating compound capable of generating a detectable signal; f) detecting HIV-2 antibody which may be present in the test sample by detecting a signal generated by the signal-generating compound, presence of the signal indicating presence of HIV-2 antibody in the test sample; g) contacting the test sample with at least one monoclonal antibody which specifically binds to Human Immunodeficiency Virus-1 protein 24 and Human Immunodeficiency Virus-2 protein p26 for a time and under conditions sufficient for the formation of antibody/antigen complexes; h) adding a conjugate to the resulting antibody/antigen complexes for a time and under conditions sufficient to allow the conjugate to bind to the bound antigen, wherein the conjugate comprises an antibody attached to a signal-generating compound capable of generating a detectable signal; and i) detecting presence of antigen which may be present in said sample by detecting a signal generated by the signal-generating compound, presence of the signal indicating presence of at least one antigen selected from the group consisting of HIV-1 antigen and HIV-2 antigen in the test sample. Again, the preferred pairs of monoclonal antibodies which may be used in the assay are described above; however, other pairs may also be utilized.

BRIEF DESCRIPTION OF THE DRAWINGS

FIG. 1a illustrates amino acid sequence alignment of p24 from HIV-1 group M and HIV-1 group O. Structural features (e.g., helices A-J) determined from group M p24 structure are shown above the sequence alignment. Synthetic group M and group O p24 peptides for mapping studies were designed and labeled according to group M or O sequence and numbering respectively.

FIG. 1b illustrates amino acid sequence alignment of p24 from HIV-1 group M, HIV-1 group O, and HIV-2 p26.

DETAILED DESCRIPTION OF THE INVENTION

Figures 2, 2A, 3:
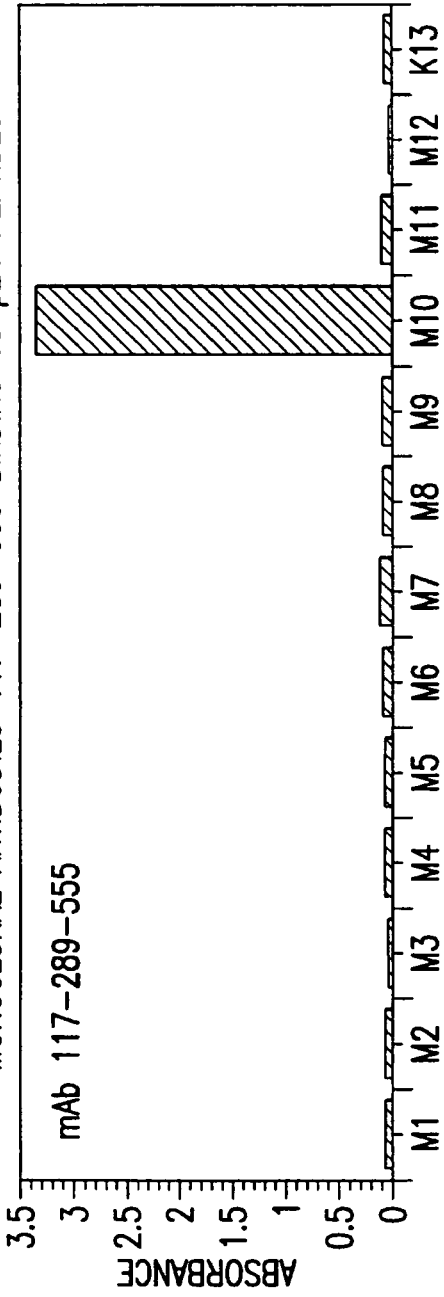
FIGS. 2a and 2b illustrate the binding of monoclonal antibodies 103-350, 117-289, 115-303, 120A-270, and 115B-151 to p24 synthetic peptides.
FIG. 3 illustrates the location of deletion clones derived from p24 of HIV-1 group M and O.

The present invention relates to novel monoclonal antibodies to HIV-1 protein p24 and HIV-2 protein p26, methods for using these monoclonal antibodies, and kits containing these antibodies. More specifically, the present invention relates to monoclonal antibodies referred to herein as 120A-270 (e.g., clone 108), 115B-151 (e.g., clone 423), and 117-289 (e.g., clone 555).

Additionally, the present invention includes monoclonal antibodies referred to herein as 103-350 (e.g., clone 474), 108-394 (e.g., clone 470) and 115B-303 (e.g., clone 620).

The present invention not only includes the monoclonal antibodies referred to above but also includes the novel hybridomas cell lines which produce these antibodies. More specifically, the cell line PTA-3980 (deposited with the American Type Culture Collection, 10801 University Boulevard, Manassas, Va. 20110 under the terms of the Budapest Treaty on Dec. 4, 2001) produces monoclonal antibody 120A-270, the cell line PTA-2809 produces monoclonal antibody 115B-151, the cell line PTA-2806 produces monoclonal antibody 117-289, the cell line PTA-2808 produces monoclonal antibody 103-350, the cell line PTA-2807 produces monoclonal antibody 108-394, and the cell line PTA-2810 produces monoclonal antibody 115B-303. The cell lines producing the last five antibodies noted were deposited with the American Type Culture Collection, 10801 University Boulevard, Manassas, Va. 20110 under the terms of the Budapest Treaty on Dec. 13, 2000 and were accorded the ATCC accession numbers noted above.

The monoclonal antibodies of the present invention or fragments thereof may be used in immunoassays for the detection of HIV-1 (Groups M and O) and HIV-2, simultaneously. (For purposes of the present invention, a "fragment" is defined as a subunit of the monoclonal antibody which reacts in the same manner, functionally, as the full antibody with respect to binding properties.) In particular, when monoclonal antibodies 120A-270 and 115B-151, or monoclonal antibodies 117-289 and 115B-151 are used in combination in an immunoassay, for example, in a sandwich assay, one may minimally detect core antigen (p24) from subtypes A, B, C, D, E, F, G and O of HIV-1 groups M and O, and HIV-2 core antigen (p26) in a patient sample. In fact, less than 25 picogram (i.e., picogram core antigen/ml of serum or plasma) quantities of the HIV-1 p24 antigen and HIV-2 p26 antigen may be detected using the combinations of monoclonal antibodies described above. Thus, the monoclonal antibodies of the present invention have a high degree of sensitivity as well as broad specificity. In particular, the unique property of these antibodies is that they recognize related, but non-identical, core antigens with approximately equivalent affinity (i.e., equivalent quantitative sensitivity), indicating that they recognize unpredictable shared epitopes, and thus exhibit shared reactivity, rather than typical and expected cross-reactive epitopes and thus exhibiting cross-reactivity. (For purposes of the present invention, "cross-reactivity" is defined as the binding of an antibody to structurally different determinants on different antigens. Antibody affinity for a cross-reactibe epitope (i.e., antigen) is lower than that for the immunogenic epitope (i.e., antigen) or shared epitope. "Shared reactivity" is defined as the binding of an antibody to structurally identical determinants on different antigens. Antibody affinity for a shared epitope is equivalent to the affinity for the immunogenic epitope (i.e., immunogen).) It should also be noted that the pairs of monoclonal antibodies are compatible, that is, each monoclonal antibody of the pair maps to a different epitope or antigenic determinant on the core protein(s). Binding of one antibody of the pair does not interfere with binding of the second antibody of the pair.

In one embodiment of the invention, the preferred embodiment, monoclonal antibody 120A-270 or a fragment thereof is coated onto a solid phase (e.g., a microparticle, a microtiter well, a bead, etc.); however, 115B-151 or 117-289 may also be used or fragments thereof. The test sample is then contacted with the monoclonal antibody or fragment thereof such that, if p24 antigen or p26 antigen is present in the patient sample, antibody/antigen complexes are then formed as a first mixture. (For example, both monoclonal antibody/p24 antigen and monoclonal antibody/p26 antigen complexes may be formed if the patient has both HIV-1 and HIV-2.) One then adds a conjugate comprising (a) a probe antibody, for example, monoclonal antibody 11B-151 (which binds an epitope distinct from and compatible with the epitope bound by 120-270) attached to (b) a signal-generating compound. Antibody/antigen/antibody probe complexes are then formed as a second mixture. HIV-1 and/or HIV-2 antigen is then detected in the sample by detecting the presence of the signal generated and thus the antibody/antigen/antibody probe complexes. The amount of antigen(s) in the test sample may also be calculated, as the signal generated is proportional to the amount of antigen in the sample.

Another manner of detecting the complexes formed is to utilize a conjugate comprising a third antibody attached to a signal-generating compound. In particular, once the antibody/antigen/antibody complexes described above have formed (i.e., the latter antibody being the $2^{nd}$ antibody which is unlabelled), one may then add a conjugate which binds to the "$2^{nd}$" unlabelled antibody in solution. The conjugate may comprise, for example, an antigen or anti-antibody capable of binding to the bound second antibody (e.g., anti-115B-151 antibody or an antibody to the probe antibody) attached to a signal-generating compound capable of generating a detectable signal. Detection of the signal thus indicates presence of the complexes and thus presence of the antigen in the sample. The signal generated is actually proportional to the amount of antigen present in the sample. (See, e.g., U.S. Pat. No. 6,015,662.) The design of the assay is dependent upon the affinities and specificities of the antibodies used, accuracy of results obtained, convenience, the nature of the solid phase, etc. (See U.S. Pat. No. 5,104,790 for a discussion of different antigen assay formats.) Additionally, it should also be noted that the initial capture antibody used in the immunoassay may be covalently or non-covalently (e.g., ionic, hydrophobic, etc.) attached to the solid phase. Linking agents for covalent attachment are known in the art and may be part of the solid phase or derivatized to it prior to coating. Examples of solid phases used in immunoassays are porous and non-porous materials, latex particles, magnetic particles, microparticles, beads, membranes, microtiter wells and plastic tubes. The choice of solid phase material and method of labeling the antigen or antibody present in the conjugate, if desired, is determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is in itself detectable or may be reacted with one or more additional compounds to generate a detectable product. Examples of signal-generating compounds include chromogens, radioisotopes (e.g., 125I, 131I, 32P, 3H, 35S and 14 C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Another type of assay in which the present monoclonal antibodies may be utilized involves simultaneously contacting: 1) one monoclonal antibody (bound to a solid support), 2) the test sample and 3) an indicator reagent comprising a monoclonal antibody or fragment thereof (e.g., 115B-151, which specifically binds to HIV-1 and HIV-2 antigen) to which a signal generating compound is attached, to form a mixture. The mixture is then incubated for a time and under conditions sufficient to form antibody/antigen/antibody complexes. The presence, if any, of HIV-1 and/or HIV-2 antigen present in the test sample and captured on the solid phase is determined by detecting the measurable signal generated by the signal-generating compound. The amount of antigen present in the test sample is proportional to the signal generated. In this assay or those described above, the monoclonal antibodies of the present invention may be used either as the capture phase or as part of the indicator reagent in solution (i.e., the reagent comprising an antibody and a signal-generating compound) Such diagnostic procedures, including those described above and below, are well-known in the art (see Immunological Methods, Vols. I and II, 1979 and 1981, Eds., Lefkovits and Pernis, Academic Press, New York; Monoclonal Antibodies, 1982, eds., Kennett et al., Plenum Press, New York; and Handbook of Experimental Immunology, 1978, ed., Weir, Blackwell Scientific Publications, St. Louis, Mo.).

It should be noted that the monoclonal antibodies of the present invention preferably may be used either alone, as a single capture antibody, or alone as a single probe and/or conjugated antibody. However, they may also be used in pairs or in trios in the assays described above. Further, combinations of the monoclonal antibodies of the present invention (and fragments thereof) may be used with other monoclonal antibodies that have specificities for epitopes of HIV-1 and/or HIV-2, other than the epitope specificities of the monoclonal antibodies of the present invention. Thus, the present monoclonal antibodies may act as components in a mixture or "cocktail" of HIV-1 and/or HIV-2 antibodies. Thus, for example, this cocktail can include a monoclonal antibody of the present invention which detects p24 of HIV-1 and p26 of HIV-2 (e.g., 120A-270) and a monoclonal antibody which detects a HIV envelope antigenic determinant in the transmembrane protein or extracellular glycoprotein. In this manner, one may be able to detect several antigenic determinants from different proteins of one or more viruses (e.g., HIV-1 and HIV-2) simultaneously.

Also, it should be noted that the monoclonal antibodies of the present invention may be utilized in a combination assay which detects: 1) antigens, such as those described above (e.g., p24 and p26) and 2) antibodies to HIV (by use of, for example, envelope antigens (e.g., HIV-1 group M and O gp41 and HIV-2 gp36). Any such combination assay, which utilizes the monoclonal antibodies of the present invention, is considered to be within the scope of the invention.

Examples of biological fluids which may be tested by the above immunoassays include plama, serum, cerebrospinal fluid, saliva, tears, nasal washes or aqueous extracts of tissues and cells. The test samples may also comprise inactivated whole virus or partially purified or recombinant p24 or p26 antigen.

It should also be noted that the above-referenced monoclonal antibodies may be used, when appropriately labeled, as competitive probes against HIV-1 and -2 core antibodies in serum samples for binding to recombinantly-derived HIV-1 p24 and HIV-2 p26.

Additionally, the monoclonal antibodies of the present invention or fragments thereof may be used in detection systems using fixed cells or fixed tissues, with appropriate labeling of each monoclonal antibody. In particular, the tissue sample is contacted with a conjugate comprising a signal-generating compound attached to one of the monoclonal antibodies of the present invention in order to form a mixture. The mixture is then incubated for a time and under conditions sufficient for antigen/antibody complexes to form. The presence of antigen present in the sample is determined by detecting the signal generated. The antibodies may also be utilized for purifying HIV-1 p24 antigen and HIV-2 p26 antigen by, for example, affinity chromatography.

Furthermore, the antibodies of the invention may be bound to matrices and used for the affinity purification of specific HIV-1 and/or HIV-2 antigens from, for example, cell cultures, or biological tissues such as blood and liver. The monoclonal antibodies, for example, may be attached to or immobilized on a substrate or support. The solution containing the HIV antigenic determinants is then contacted with the immobilized antibody for a time and under conditions suitable for the formation of immune complexes between the antibody and polypeptides containing the p24 and p26 determinants. Unbound material is separated from the bound immune complexes. The complexes or antigenic fragments are then separated from the support.

One or more of the monoclonal antibodies of the present invention, and preferably the pairs suggested above, is particularly suitable for use in the form of a kit. The kit may comprise one or more containers such as vials or bottles, with each container containing a pair of the monoclonal antibodies, or as cocktails of monoclonal antibodies. These kits may also contain vials or containers of other reagents needed for performing the assay, such as washing, processing and indicator reagents.

Additionally, the present invention also includes a vaccine comprising one or more of the monoclonal antibodies of the present invention and a pharmaceutically acceptable adjuvant (e.g., Freund's adjuvant) which can be administered to HIV-infected individuals (i.e., passive immunization). Furthermore, the monoclonal antibodies of the present invention can serve prophylactically for administration to non-infected, high-risk individuals, such as health care workers.

It should also be noted that the monoclonal antibodies of the present invention may also serve as research tools for epitope mapping of HIV proteins p24 and p26. Further, it should be noted that not only do the monoclonal antibodies of the present invention bind to proteins and protein precursors of HIV clinical isolates which contain the targeted region or regions of antigenic determinants, in addition, the antibodies bind to recombinant proteins and synthetic analogues of the proteins which contain the antigenic determinant(s). Thus, for example, the monoclonal antibodies of the present invention may be used in binding experiments involving recombinant proteins and synthetic analogues of p24 of HIV-l and p26 of HIV-2.

Additionally, antibodies of the present invention which are unlabeled may be used in agglutination assays or can be used in combinantion with labeled antibodies that are reactive with the monoclonal antibody, such as antibodies specific for immunoglobulin.

The present invention also comprises a method for treating a mammal infected with HIV-1 and/or HIV-2 comprising administering to a mammal, in need of such treatment, an effective amount of one of more of the monoclonal antibodies of the present invention in the form of a pharmaceutical composition, as described directly below. A pharmaceutically effective amount means any amount of the compound which, when incorporated in the pharmaceutical composition, will be effective to inhibit HIV replication and thereby treat Acquired Immunodeficiency Syndrome (AIDS) but less than an amount which would be toxic to the subject.

Additionally, the present invention encompasses pharmaceutical compositions comprising one or more of the monoclonal antibodies of the present invention and a pharmaceutically acceptable carrier. A pharmaceutical carrier is any compatible, non-toxic substance suitable to deliver one or more monoclonal antibodies to the patient. For example, sterile water, alchohol, fats, waxes and inert solids may be used as carriers. The composition may also contain monoclonal antibodies which bind to proteins or glycoproteins of HIV other than p24 and/or p26. Further, the pharmaceutical composition may be administered alone or in conjunction with other anti-retroviral agents. (See Mitsuya et al., *Nature* 325:773-778 (1987).) The pharmaceutical compositions of the present invention may be administered either orally or parenterally (i.e., subcutaneously, intramuscularly or intravenously).

Further, it should be noted that one or more of the monoclonal antibodies of the present invention may be used to generate chimeric antibodies for therapeutic use, for example, or as assay controls or calibrators.

Since all of the monoclonal antibodies of the present invention bind both to p24 of HIV-1 and to p26 of HIV-2, as evidenced by the data presented in Table 5, for example, any one of more of the monocloanl antibodies may be used in the diagnostic assays, kits, compositions and methods described above. Certainly those with the strongest binding specificities and capabilities (with respect to p24 and p26) are preferred.

The present invention may be illustrated by the use of the following non-limiting examples:

EXAMPLE 1

Immunogen Selection

The immunization strategies included HIV-1 group O and HIV-1 group M antigens to drive the immune response toward recognition of both shared epitopes within the core antigens of both groups of HIV-1. Three different HIV-1 immunogens were used in various combinations to develop an anti-HIV-1 p24 response in the animal host. Two HIV-1 group M antigens manufactured at Abbott Laboratories (Abbott Park, Ill.) were derived from denatured whole viral lysates while native HIV-1 group M p24 (p24M) protein was purified from the viral lysates.

The third immunogen was a recombinant p24 antigen (rp24-O) derived from the gag gene of HIV-1 group O isolate HAM112. The p24 gene from HAM112 was cloned into the lambda PL vector and expressed in *E. coli*. The construction, scale up and purification of the recombinant antigen were performed according to published methods for recombinant proteins made in *E. coli*. (Seetharam, R. and Sharma, S. K., (eds), 1991. '*Purification and Analysis of Recombinant Proteins*', Marcel Dekker. New York, N.Y.) Verification of the amino acid sequence against published results confirmed integrity of the product. (Van den Haesevelde et al., 1994. *Genomic cloning and complete sequence analysis of a highly divergent African human immunodeficiency virus isolate*. J. Virol. 68:1586.)

EXAMPLE 2

Immunization of Mice

The animal models selected for hybridoma development were three strains of mice, the CAf1, the RBf/dn, and the BALB/c. The mice were females, age 6-8 weeks old, purchased from Jackson Laboratory (Bar Harbor, Me.). In order to produce anti-HIV-1 p24 monoclonal antibodies with high affinity, two different immunization strategies were utilized. Hybridomas secreting anti-p24 monoclonal antibodies (Mab) 103-350-474, 108-394-470, 115B-303-620, 115B-151-423, and 117-289-555 were produced from mice which were immunized twice with rp24-O or p24-M or mixture of both rp24O and p24M subcutaneously (s.c.) or intramuscularly (i.m.). The mice were rested for 4-12 months for affinity maturation and boosted intrasplenically (i.s.) with immunogen three days prior to fusion. 120A-270-108 was produced from a BALB/c mouse that was hyperimmunized weekly six times with low dosage of purified native p24-M given alternatively between intraperitoneal (i.p.) administration and subcutaneous administration.

The immunization procedures are described in detail as follows:

Hybridoma 103-350-474 was produced from cell fusion #103. On day 1, CAF1 mouse #1555 received 10 ug of rp240 antigen in 0.2 ml of Freund's Complete Adjuvant (CFA) (Difco Laboratories, Detroit, Mich.) given subcutaneously. On day 56, the mouse received 10 ug of rp24O antigen in 0.2 ml of Incomplete Freund's Adjuvant (IFA) (Difco Laboratories, Detroit, Mich.) given intramuscularly (i.m.). On day 74, the mouse was bled for assessment of anti-HIV-1 antibody titer by indirect enzyme-linked immunoassay (EIA). On day 186, the mouse was boosted i.s. with 25 ug of HIV-1 group M viral lysate in normal saline.

Hybridoma 108-394-470 was produced from cell fusion #108. On day 1, CAF1 mouse #1556 received 10 ug of rp24O antigen in 0.2 ml of CFA given s.c. On day 56, the mouse received 10 ug of rp24O antigen in 0.2 ml of IFA given i.m. On day 74, the mouse was bled for assessment of anti-HIV-1 antibody titer by indirect EIA. On day 270, the mouse was boosted i.s. with 45 ug of purified native HIV-1 group M p24 in normal saline.

Hybridomas 115B-151-423 and 115B-303-620 were produced from cell fusion #115B. On day 1, CAF1 mouse #1563 received 10 ug of rp24O antigen in 0.2 ml of CFA given s.c. On day 210, the mouse received mixture of 10 ug of rp24O and 10 ug of p24M in 0.2 ml of IFA given s.c. On day 235, the mouse was bled for assessment of anti-HIV-1 antibody titer by indirect EIA. On day 375, the mouse was boosted i.s. with a mixture of 10 ug of rp24O and 10 ug of p24M in normal saline.

Hybridoma 117-289-555 was produced from cell fusion #117. On day 1, RBf/dn mouse #1545 received 10 ug of rp24O antigen in 0.2 ml of CFA given s.c. On day 56, the mouse received mixture of 10 ug of rp24O in 0.2 ml of IFA given i.m. On day 74, the mouse was bled for assessment of anti-HIV-1 antibody titer by indirect EIA. On day 392, the mouse was boosted i.s. with a mixture of 45 ug of rp24O and purified native p24M in normal saline. Hybridoma 120A-270-108 was produced from cell fusion #120A of a hyperimmunized BALB/c mouse #7 which received 0.2 ml of immunogen containing 10 ug of purified native p24M antigen and 4 ug of *S. typhimurium* extract (RIBI Immunochemicals, RiBi Immuno Chem Research, Hamilton, Mont.) given i.p. on day 1, s.c. on day 7, and i.p. on day 14. On day 21, the mouse was bled for assessment of anti-HIV-1 p24 antibody titer by indirect EIA. On days 28, 35, and 42, the mouse received 5 ug of purified native p24M antigen in 0.2 ml of RIBI adjuvant given s.c., i.p., and s.c., respectively. On day 49, the mouse was bled a second time for assessment of anti-HIV-1 antibody titer by indirect EIA. On day 77, three days before fusion, the mouse was boosted i.s. with 50 ug of purified native p24M antigen in normal saline.

EXAMPLE 3

Assessment of Anti-p24 Antibody Titer of the Immunized Mice

Indirect binding and direct sandwich enzyme-linked immunoassays (EIA) were used to assess anti-HIV-1 antibody titers from the immunized mice. (Direct sandwich EIA was performed with a limited amount of core antigen to detect only high affinity antibodies.) Sera from naive or immunized mice were serially diluted in 10 mM sodium phosphate buffer (PBS), pH 7.4, containing 5% bovine serum albumin (BSA) and 0.03% sodium azide as preservative. The detailed assay procedures are described below. The assessment of anti-p24 antibody titers from the immunized mice is shown in Table 1a from the indirect binding EIA and Table 1b from the direct sandwich EIA.

TABLE 1a

Assessment of anti -p24 antibody titers by indirect EIA

| Fusion # | Animal ID | Sera dilution | A490 nm reading | | |
|---|---|---|---|---|---|
| | | | rp24-O | p24-M | BSA control |
| 103 | CAf1 #1555 | 1/24,300 | 1.219 | 1.156 | 0.008 |
| 108 | CAf1 #1556 | 1/24,300 | 1.157 | 1.109 | 0.005 |
| 117 | RBf/dn #1545 | 1/900 | 0.462 | 0.600 | 0.019 |
| 120A | BALB/c #7 | 1/100,000 | NT | 1.709 | 0.025 |
| | Pre-bled ms serum | 1/900 | 0.036 | 0.093 | 0.018 |

TABLE 1b

Assessment of anti -p24 antibody titers by direct sandwich EIA

| Fusion # | Animal ID | Sera dilution | A490 nm reading | |
|---|---|---|---|---|
| | | | M lysate | O lysate |
| 115B | CAf1 #1563 | 1/8,100 | 0.540 | 0.401 |
| 120A | BALB/c #7 | 1/1,000 | 1.579 | 0.762 |
| | Pre-bled ms serum | 1/1,000 | 0.163 | 0.162 |

For the direct binding EIA, briefly, the diluted sera were reacted with microtiter wells directly coated with 100 ul of 3 ug/ml in PBS of p24M (i.e., p24 from group M) or rp24O (i.e., recombinant p24 from group) antigen or mixture of p24M and rp24O and then blocked with 2% bovine serum albumin (BSA) in PBS. After 1 hour incubation at room temperature (RT) on a mirotiter plate shaker (Lab-Line Instruments, Melrose, Ill.), the plate was washed 3 times with distilled water using a microtiter plate washer (Skanwash, Skatron Instruments, Sterling, Va.). One hundred ul of 0.2 ug/ml of goat ant-mouse IgG+IgM-Horseradish Peroxidase (HRPO) (KPL, Gaithersburg, Md.) conjugate were added to each well of the plate. After incubating 30 minutes at RT, the plate was washed 3 times (as above). Enzyme substrate o-phenylenediamine:2HCl (OPD) solution was added to each well to develop a color reaction for 5 minutes in the dark at RT. The reaction was stopped by addition of 1N $H_2SO_4$ into each well. The plate was read at A490 nm in a microtiter plate reader (Titertek multiwell EIA reader, ICN, Huntsville, Ala.).

For the indirect sandwich EIA, a microtiter wells were coated with 100 ul per well of 10 ug/ml in PBS of goat anti-mouse IgG+M antibodies (KPL) overnight at 2-8 C. The plate was washed 3 times with distilled water using a plate washer (Skanwash, Skatron Instruments, Sterling, Va.) and then blocked with 2% BSA in PBS for 30 minutes at RT. One hundred ul portions of culture fluids were added to the wells, and the plate was incubated for 1 hour at RT on a plate shaker. Anti-p24 antibodies secreted in culture fluids were captured by goat anti-mouse IgG+M coated on solid phase. After washing, 100 ul portions of 100 pg/ml of HIV-1 viral lysate were added into each well and the plate was incubated for one hour at RT on a plate shaker. After washing, 100 ul portions of 0.5 ug/ml of rabbit anti-p24 antibodies were added into each well and the plate was incubated for one hour at RT on a plate shaker. After washing, 100 ul of 0.2 ug/ml of goat anti-rabbit IgG-HRPO (KPL) were added to each well, and the plate was incubated for 30 minutes at RT. After the final washing, chromogen OPD was added as described above.

EXAMPLE 4

Cell Fusion

Three days after the pre-fusion antigen boost, mice were sacrificed and their spleens were disrupted to single cells. The single cell suspensions were treated with 0.83% $NH_4Cl$ to remove red blood cells, and then mixed with SP2/0 cells at a 10:1 ratio of SP2/0:spleen cells. The mixed cells were centrifuged, washed once with serum-free medium, then centrifuged again. The supernatant was removed from the cell pellet. The fusogen, polyethylene glycol (PEG), was used to form hybrids of immune spleen cells with myeloma cell line SP2/0 (HPRT neg.) [Kohler and Milstein, Nature (1975) 256:494, and reviewed in Monoclonal Hybridoma Antibodies: Techniques and Applications ed. Hurrell (CRC Press, Inc., 19820]. Briefly, fusion of spleen cells and SP2/0 cells was accomplished by exposing the pellet to 40% PEG (M.W. 1450, American Type Culture Collection, Manassas, Va.) in serum-free Iscoe's Modified Dulbecco's Medium (IMDM) for two minutes. The PEG and cell suspension was diluted slowly by the addition of 20 ml of serum free IMDM over a period of five minutes, followed by collection of the cells by centrifugation. The supernatant was decanted and replaced with 30 ml IMDM containing 20% fetal bovine serum (Hyclone, Logan, Utah) with HAT (hypozanthine, aminopterin, and thymidine) to select for hybridomas. Spleen cells from one nonimmunized BALB/c mouse also were added as a feeder layer. The cells were plated at 0.1 ml/well in three 96 well tissue culture plates. Three days later an additional 0.1 ml of HAT media was added to each well. At weekly intervals thereafter, one half of the media was replaced with IMDM containing 20% fetal bovine serum with HAT, and hybrids were allowed to grow an additional 7-14 days.

Some of the hybrids were composed of spleen cells, making antibody to HIV-1, fused with SP2/0 cells. Briefly, the fusogen promotes fusion of spleen cell and SP2/0 cell membranes, forming a heterokaryon containing nuclei of both cells. Eventually, the dissimilar nuclei fuse producing a single nucleus capable of synchronous mitosis. As the fused cells divide, the hybrid stabilizes by losing chromosomes of each nucleus. The fused cells were plated into multiple 96 well plates at $10^5$ to $10^6$ cells per well. Hybrid cells formed from SP2/0:spleen cell fusions were selectively propagated by culturing in HAT medium. All unfused SP2/0 or SP2/0:SP2/0 fused cells were prevented from growing by aminopterin, and unfused spleen cells or spleen:spleen fused cells died off in culture. Only spleen cell:SP2/0 hybrids will grow in the HAT selection medium.

EXAMPLE 5

Screening, Cloning and Characterization of p24 Monoclonal Antibodies

After 10-14 days, culture fluids from wells containing hybridoma cell growth were screened for antibody to HIV-1 p24. The indirect EIA was used to screen the culture fluids from cell fusions #103, #108, #115B, and #117. In order to select anti-HIV core protein monoclonal antibodies with high affinity, a direct sandwich EIA assay was also utilized to screen potentially useful clones from cell fusions #120A and cloning of fusions #115B and 120A. Both direct and indirect EIAs are described in the section of antisera titer assessment of Example 2. The primary screening data from the hybridomas described in this application are shown in Table 2a and 2b.

TABLE 2a

Primary Fusion screened by indirect binding EIA

| | | A490 nm reading | |
|---|---|---|---|
| Hybrid # | HIV Ag used | Sample | Blank control |
| 103-350 | p24-M lysate | 0.921 | 0.030 |
| 108-394 | p24-M lysate | 0.497 | 0.000 |
| 115B-151 | p24-M lysate | 0.662 | 0.012 |
| 115B-303 | p24-M lysate | 0.467 | 0.003 |
| 117-289 | p24-M lysate | 0.295 | 0.000 |

TABLE 2b

Primary Fusion screened by direct sandwich EIA

| | | A490 nm reading | |
|---|---|---|---|
| Hybrid # | HIV Ag used | Sample | Negative control |
| 120A-270 | p24-M lysate | 0.501 | −0.011 |

Hybridomas showing strong positive signal in the primary screening EIAs were transferred into 24-well plates for cell expansion. Culture fluids were again assayed for the presence of anti-p24 antibody. Anti-p24 positive hybrids were further expanded in T25 flask for cloning by limiting dilution. Each expanded-hybrid was plated in a 96-well plate at a dilution of $10^5$ to $10^6$ and allowed to grow 10-21 days. Culture fluids from limiting dilution were assayed for the presence of anti-p24 antibody. The hybridoma designation is based on a numbering system using 3 numbers: the first being the fusion number, the second is the parental hybrid number and the third is the subclone number. Each 96-well tissue culture plate is sequentially numbered 1 to 96. For example, hybridoma #103-350-474 originates from the $103^{rd}$ fusion. The parental hybrid is #350 as it derives from the $3^{rd}$ fusion plate in well #50. The subclone is #474 since it is from the $4^{th}$ cloning plate, well #74. The clones were obtained by limiting dilution using the guidelines outlined by J. W. Goding in *Monoclonal Antibodies: Principles and Practice* (Academic Press, N.Y., 1983). The primary cloning data for the hybridomas described in this application are shown in Table 3a and 3b.

TABLE 3a

Primary clone screened by indirect binding EIA

| | | A490 nm reading | |
|---|---|---|---|
| Clone # | HIV Ag used | Sample | Blank control |
| 103-350-474 | p24-M lysate | 0.489 | 0.021 |
| 108-394-470 | p24-M lysate | 0.466 | 0.000 |

TABLE 3b

Primary clone screened by direct sandwich EIA

| | | A490 nm reading | |
|---|---|---|---|
| Clone # | HIV Ag used | Sample | Blank control |
| 115B-151-423 | p24-M lysate | 0.846 | 0.000 |
| 115B-303-620 | p24-M lysate | 0.991 | 0.006 |
| 117-289-555 | p24-M lysate | 0.830 | 0.011 |
| 120A-270-108 | p24-M lysate | 0.371 | −0.021 |

The isotypes of anti-p24 Mabs were determined with the SBA Clonotyping System (Southern Biotechnology Associates, Inc., Birmingham, Ala.). Briefly, microtiter wells plate were coated with 100 ul portions of goat anti-mouse IgG+M antibodies (KPL) for 18-24 hours at 2-8 C. The wells were washed and blocked with 2% BSA in PBS for 30 minutes at RT. After washing, 100 ul portions of culture fluids were added into the wells and incubated for 2 hour at RT on a plate shaker. After washing, 100 ul portions of rabbit anti-mouse isotype-specific antibodies were added to the wells and incubated for one hour at RT on a plate shaker. After washing, 100 ul of goat anti-rabbit IgG-HRPO (KPL) were added to the wells and incubated for another 30 minutes at RT on a plate shaker. After the final washing, chromagen OPD was added as described above. The isotypes of Mabs 103-350-474, 108-394-470, 115B-151-423, 115B-303-620, 117-289-555, and 120A-270-108 are summarized in Table 4.

TABLE 4

Monoclonal antibody isotypes

| Mab ID | Isotype | Light chain |
|---|---|---|
| 103-350-474 | IgG2a | kappa |
| 108-394-470 | IgG2b | kappa |
| 115B-151-423 | IgG1 | kappa |
| 115B-303-620 | IgG2b | kappa |
| 117-289-555 | IgG1 | kappa |
| 120A-270-108 | IgG1 | kappa |

The specific reactivities of Mabs to HIV-1/2 antigens were tested in the direct sandwich EIA as described in the previous section. The results are summarized in Table 5.

TABLE 5

Reactivities of anti -HIV-1 p24 Mabs with HIV-1/2 p24/p26

| | Reactivity with | | |
|---|---|---|---|
| Mab ID | p24-M | p24-O lysate | HIV-2 lyaste |
| 103-350-474 | ++ | ++ | ++ |
| 108-394-470 | ++ | ++ | + |
| 115B-151-423 | ++ | ++ | ++ |
| 115B-303-620 | ++ | ++ | ++ |
| 117-289-555 | ++ | ++ | ++ |
| 120A-270-108 | ++ | ++ | ++ |

++ = Very Strong

In view of the results presented in Table 5, all of the monoclonal antibodies of the present invention react with HIV-1/2 p24/p26 antigens. (HIV-1 group O and HIV-2 NIH-Z viral lysates were purchased from ABI (Gaithersburg, Md.).)

EXAMPLE 6

Antibody Production and Purification

In order to produce large amounts of Mabs for further characterization and testing, anti-p24 hybridoma cell lines were further expanded in T250 flasks and weaned to serum free media, H-SFM (Life Technologies, Grand Island, N.Y.). When the hybridoma cell lines were adapted to H-SFM, they were seeded in roller bottles for large scale antibody production. Culture fluids were harvested from the roller bottles and concentrated by a filtration system. The roller bottle derived antibody was purified on a Protein A column from PerSeptive Biosystems (Cambridge, Ma.).

EXAMPLE 7

Affinity Measurement of Anti-p24 Monoclonal Antibodies

Affinities of purified anti-p24 Mabs 103-350-474, 108-294-470, 115B-303-620, 115B-151-423, 117-289-555, and 120A-270-108 were measured by a surface plasma resonance (SPR) based BIAcore immunosensor instrument (Pharmacia, Uppsala, Sweden). Briefly, goat anti-mouse IgG (Fc) antibodies were covalently coupled to amino-sensor chips by EDAC chemistry. Each mouse IgG monoclonal antibody was injected into the sensor chip and captured by the immobilzed goat anti-mouse IgG antibodies. The unbound mouse monoclonal antibody was washed away from the chip. A baseline measurement of surface plasma resonance (SPR) signal was recorded for each monoclonal. When purified HIV-1 p24 protein was injected into the sensor chip and reacted with anti-p24 monoclonal antibody, SPR signal started to increase. The slope of binding curve was proportional to the association constant of each monoclonal antibody. After binding was achieved, a wash step was introduced. The dissociation rate of p24 from anti-p24 monoclonal antibody was proportional to the decrease of SPR signal. After each cycle of measurement, HCl buffer was applied into the sensor chip to remove anti-p24 monoclonal antibody from the sensor chip for the next measurement. Based upon the on-rate and off-rate SPR signals, association (Ka), dissociation (Kd), and relative affinity (K)-constants of each monoclonal antibody were determined. The data are summarized in Table 6.

TABLE 6

| | Binding constants | | |
|---|---|---|---|
| Clone # | $Ka(M^{-1}s^{-1})$ | $Kd(s^{-1})$ | $K(M^{-1})$ |
| 103-350-474 | $8.3 \times 10e5$ | $5.1 \times 10e-4$ | $1.6 \times 10e9$ |
| 108-394-470 | $8.1 \times 10e5$ | $4.2 \times 10e-4$ | $1.9 \times 10e9$ |
| 115B-151-423 | $1.3 \times 10e6$ | $2.0 \times 10e-4$ | $6.5 \times 10e9$ |
| 115B-303-620 | $8.3 \times 10e5$ | $2.6 \times 10e-4$ | $3.2 \times 10e9$ |
| 117-289-555 | $3.5 \times 10e5$ | $3.3 \times 10e-4$ | $1.1 \times 10e9$ |
| 120A-270-108 | $8.1 \times 10e5$ | $8.8 \times 10e-4$ | $9.2 \times 10e9$ |

EXAMPLE 8

Epitope Mapping of p24 Monoclonal Antibodies

Epitopes on HIV-1 p24 recognized by mouse monoclonal antibodies were identified using two sets of thirteen p24 synthetic peptides (FIG. 1a). Peptide design was based on the three dimensional structure of p24 antigen (Gitti, et al., Science 273: 231 (1996); Gamble, et al., Science 278: 849 (1997)) in order to present selected, uninterrupted regions of helical structure (in vivo) that might be unique to shared epitopes. These peptides covered all helical regions (A-J) on the core proteins. Monoclonal antibodies were reacted against both group M (clade B) and group O (Ham112) peptides. Peptides were designated M1 to M13 representing HIV-1 group M clade B p24, or O1 to O13 representing HIV-1 group O (Ham 112 isolate) p24. Each peptide also contained an additional cysteine on its C-terminus which was reacted with maleimide-modified Keyhole Lympet Hemocyanin (KLH) to form two series of KLH conjugated peptides in addition to unconjugated peptides. KLH conjugated peptides were generated in order to help stabilize and present conformational structures that might be essential for epitope presentation and recognition (monoclonal binding). KLH conjugated peptides were designated as KM1 to KM13 for group M peptides or KO1 to KO13 for group O peptides.

Binding of monoclonal antibodies (Mabs) to sets of synthetic peptides was determined by an indirect ELISA assay. Briefly, free or KLH conjugated synthetic peptides were coated on the wells of microtiter plates. The peptide coated wells were incubated with Mabs prepared to a concentration of approximately 1 ug/ml. Bound Mabs were detected by enzyme or acridinium-labeled goat anti-mouse IgG antibodies. Representative data are depicted in FIGS. 2a and b. Epitopes recognized by Mab 103-350-474, 117-289-555, 115B-303-620 and 120A-270-108 were identified as follows:

Monoclonal antibody 103-350-474 specifically bound to the KLH conjugated group M and group O peptides # 4 (KM4/KO4), which corresponds to the helix D region of p24. The epitope is linear with apparent secondary conformational requirements. Little or no consistent binding was detected when 103-350-474 was reacted against free (un-conjugated) peptides. In contrast, when peptides were conjugated to a carrier protein (KLH) in order to promote secondary conformational peptide structures, 103-350-474 consistently exhibited strong (high S/N) binding against KM4/KO4 peptides. The epitope appears to be linear because the antibody binds small synthetic peptides, but the optimal epitope may require specific secondary helical structures. Therefore, the epitope is most broadly defined as comprising amino acids 63-89, and most narrowly estimated as requiring amino acids 63-80, which map to the helix-D region. Further, cross reactivity of the antibody between M and O p24 indicates that the p24 regions of greatest sequence homology in helix-D are most likely involved in forming the epitope. The residues in bold are most likely key to forming the epitope, but secondary structure involving or requiring neighboring amino acids cannot be excluded.

(K) M4 peptide 63-89: C<u>QAAMQ</u> <u>MLKET</u> <u>INEEA</u> <u>AEWDR</u> VHPVH AG (SEQ ID NO:1)

(K) O4 peptide 63-89: C<u>QGALQ</u> <u>VLKEV</u> <u>INEEA</u> <u>ADWDR</u> SHPPV VG (SEQ ID NO:2)

Monoclonal antibody 117-289-555 specifically bound to both group M and group O M10/O10 peptides, which correspond to the helix H region, which is part of the major homology region (MHR). The epitope appears to be linear because the antibody readily binds free (un-conjugated) M10/O10 peptides. Binding to both group M and group O p24 is expected. The residues in bold are likely key to forming the epitope.

```
M10 peptide 151-176:
  CLDIRQ GPKEP FRDYV DRFYK TLRAEQ    (SEQ ID NO:3)

O10 peptide 152-177:
  CLDIKQ GPKEP PRDYV DRFYK TLRAEQ    (SEQ ID NO:4)
```

Monoclonal antibody 115B-303-620 bound to M12 and O12 peptides, which corresponds to the helix J-K region of p24. The epitope appears to be linear based on the strong (high S/N) binding to free (un-conjugated) peptides of M12/O12. The residues in bold are likely key to forming the epitope, but secondary structure involving or requiring neighboring amino acids cannot be excluded.

```
M12 peptide:
  CKTIL KALGP AATLE EMMTA            (SEQ ID NO:5)

O12 peptide:
  CKQIL KALGP GATLE EMMVA            (SEQ ID NO:6)
```

Monoclonal antibody 120A-270-108 mapped to the helix H and MHR region of p24 Similar to monoclonal antibody 117-289-555. However, 120A-270-108 recognizes an epitope distinct from an epitope recognized by 117-289-555. The significant difference between 117-289-555 and 120A-270-108 is that 120A-270-108 only moderately bound to the KLH conjugated M10 peptide. No binding was detected when 120A-270-108 was reacted against free (un-conjugated) peptides. Thus, the optimal epitope of 120A-270-108 requires specific secondary or tertiary structures. Furthermore, 117-289-555 and 120A-270-108 belong to different compatibility groups because they bind simultaneously to core proteins without interference or competition from each other (see Table 7 below).

TABLE 7

Sandwich formation of mAbs with p24proteins (both group M and group O)

| mAbs in solid phase | Signal labeled mAbs in solution phase | | | | | |
|---|---|---|---|---|---|---|
| | 103-350-474 | 117-289-555 | 115B-303-620 | 115B-151-423 | 108-394-470 | 120A-270-108 |
| 103-350-474 | − | + | + | + | − | − |
| 117-289-555 | + | − | + | + | + | + |
| 115B-303-620 | + | + | − | + | + | + |
| 115B-151-423 | + | + | + | − | + | + |
| 108-394-470 | − | + | + | + | − | − |
| 120A-270-108 | − | + | + | + | − | − |
| 120B-580-106 helix A | + | + | + | − | +/− | − |

The + sign indicates compatibility of paired mAbs binding to p24 antigen simultaneously The compatibility study also showed that, unlike 117-289 which can pair with either Mab 103-350 or 108-394 to form a sandwich, 120A-270 cannot form a sandwich with either Mab(Table 7). The compatibility data clearly demonstrated that the epitope recognized by 120A-270 is distinct and different from the epitope recognized by 117-289. Mab 120A-270 most likely recognizes a conformational epitope, formed in part, by amino acids 151-176.

Figures 2, 2A, 3, 4:
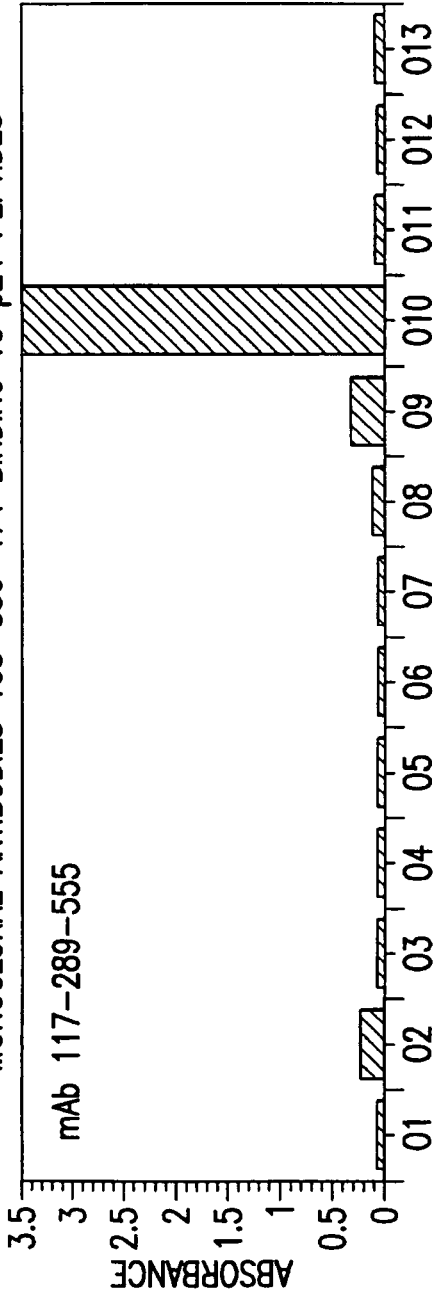
FIG. 4 illustrates the results of Western blots used to map binding of monoclonal antibodies 115B-151 and 108-394 to regions of p24.
Figures 1, 2B:
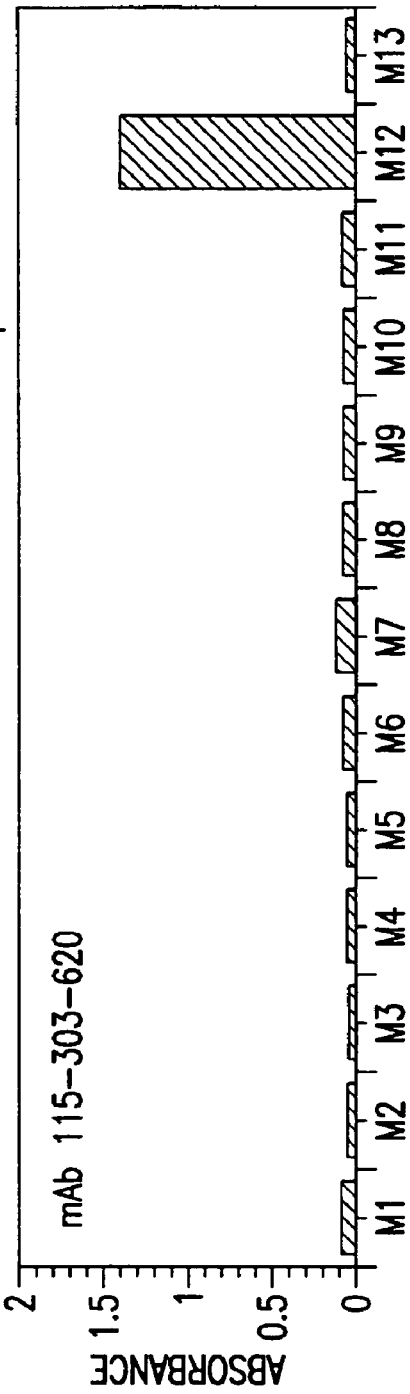
Figures 2, 2B:
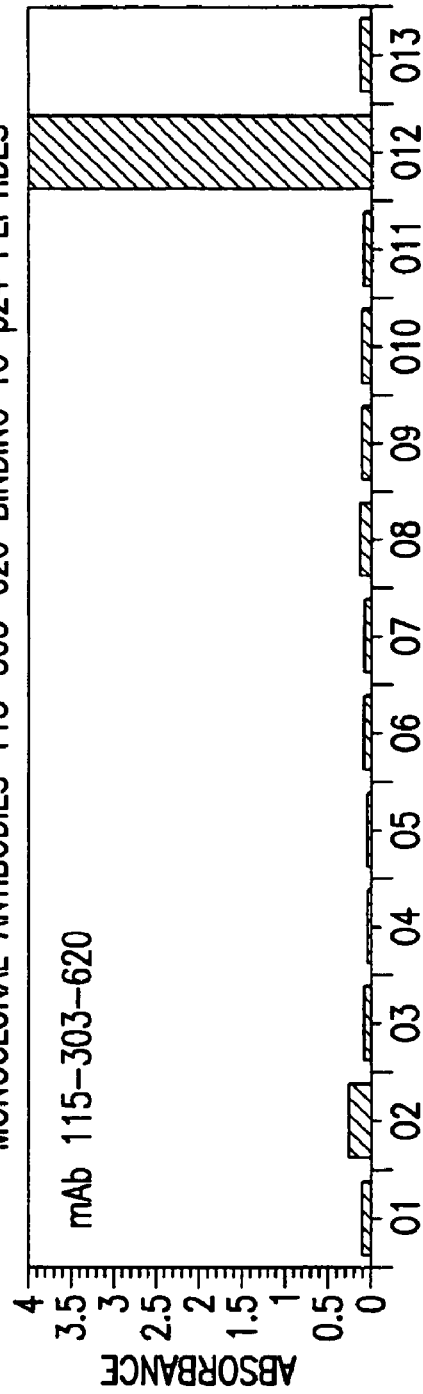
Figures 2, 2B, 3:
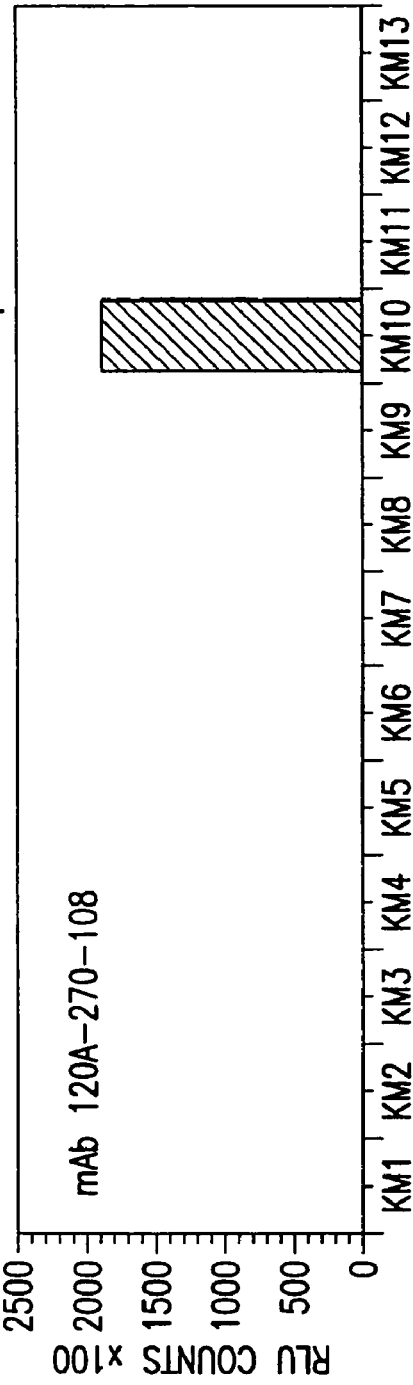
Figures 2, 2B, 3, 4:
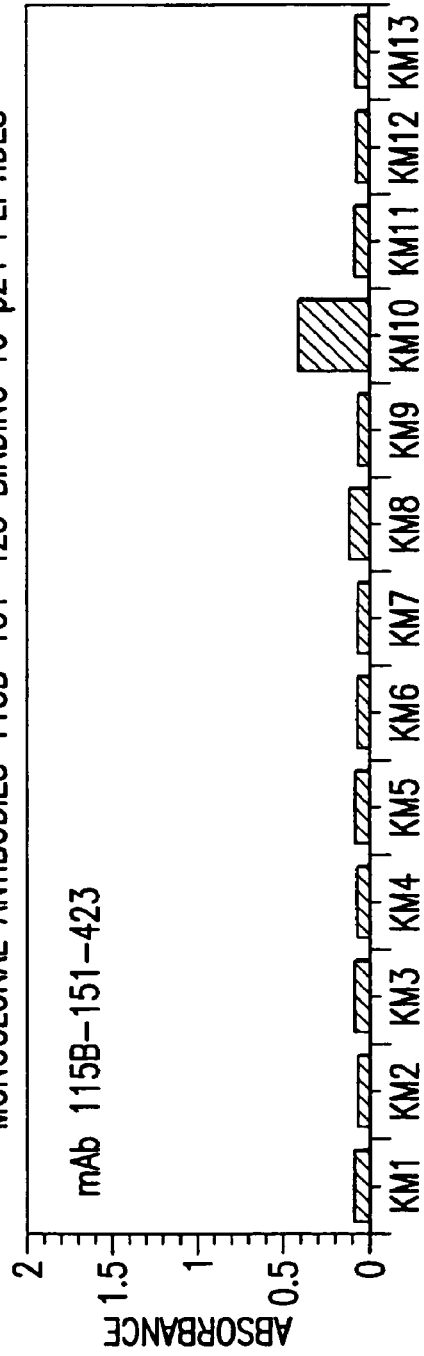

Two Mabs 115B-151 and 108-394, fail to bind free synthetic peptides, and.115B-151 weakly bound to one KLH coupled peptide (FIG. 2B). Failure to bind synthetic peptides indicated that these Mabs recognize conformational epitopes on core antigen. Conformational epitopes are formed by contiguous amino acids brought together by the tertiary or quaternary folding of p24 antigen. A tertiary or quaternary structure dependent conformational epitope generally cannot be mimicked by small synthetic peptides.

A set of large overlapping p24 polypeptides were used to locate conformational epitopes recognized by the 115B-151 and 108-394. Overlapping p24 polypeptides were expressed in *E. coli.* (rproteins) from plasmids carrying unique portions of p24 nucleotide sequence (deletion clones). Two sets of six deletion clones were designed based on the structure of p24. Specific binding of monoclonal antibodies to p24 polypeptides was determined using the Western blot method. Briefly, the expressed (recombinant) p24 polypeptides in extracts of *E. coli* were subjected to SDS-PAGE and transferred to nitrocellulose membranes. The membranes containing electrophoreticaly separated proteins were reacted with p24 Mabs (~5ug/ml concentration) and bound monoclonal antibodies were detected by enzyme labeled goat anti-mouse IgG. FIG. 4 illustrates Western blot results of Mabs 115B-151 and 108-394.

Monoclonal antibody 115B-151 specifically bound to group M polypeptides F(1-172) and G(137-231) and group O polypeptides N(1-173) and O(138-232). The overlapping region (amino acids 137-172) between F and G and N and O, may contribute to epitope recognized by 115B-151. This data is supported by weak but consistent binding of 115B-151 against the KLH conjugated synthetic peptides KM10 and KO10, which contain amino acids 137-172 (FIG. 2B). Mab 115B-151 differed from 117-289 and 120A-270 because (a) 115B-151 apparently required the epitope to be in a specific secondary or tertiary conformation, (b) it was compatible with 117-289/120A-270 to form a sandwich with p24 (Table 7), and (c) monoclonal antibodies against helix A were incompatible and strongly competed with 115B-151, but were compatible with 117-289. The strong competition of helix A directed monoclonal with 115B -151, in addition to the weak binding against KLH conjugated peptides, may indicate that the optimal epitope recognized by 115B-151 includes a portion of helix A in addition to the minimal linear epitope identified within helix H.

Monoclonal 108-394 mapped to a conformational epitope formed within the first 172/173 amino acids of M/O p24. The epitope is non-linear because HIV-1 M and O synthetic peptides, free or conjugated to carrier protein KLH, were unreactive with 108-394. In addition, 108-394 reacted only with the largest of the polypeptides (F 1-172/N 1-173) derived from M/O p24. Although M polypeptides C (1-65), E (1-130), and I (60-150), and polypeptides L (1-65), M (1-131), and Q (60-151) contain large segments of the same sequence found in polypeptides F (1-172) and N (1-173), an epitope recognized by 108-394 apparently was not formed from the shorter polypeptides. These data are consistent with a conformational epitope formed by a major portion of p24 comprising at least the first 172/173 amino acids.

Figures 2, 2B, 3, 4, 5:
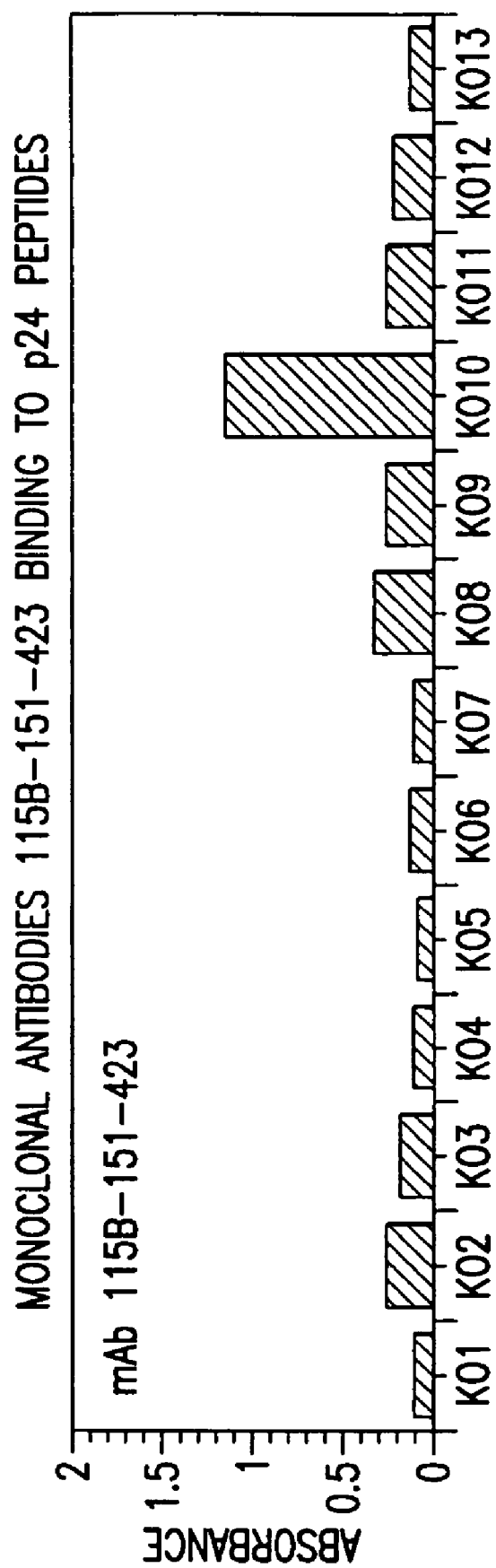
FIG. 5 summarizes HIV-1 p24 epitopes recognized by p24 monoclonal antibodies.
Figure 3:
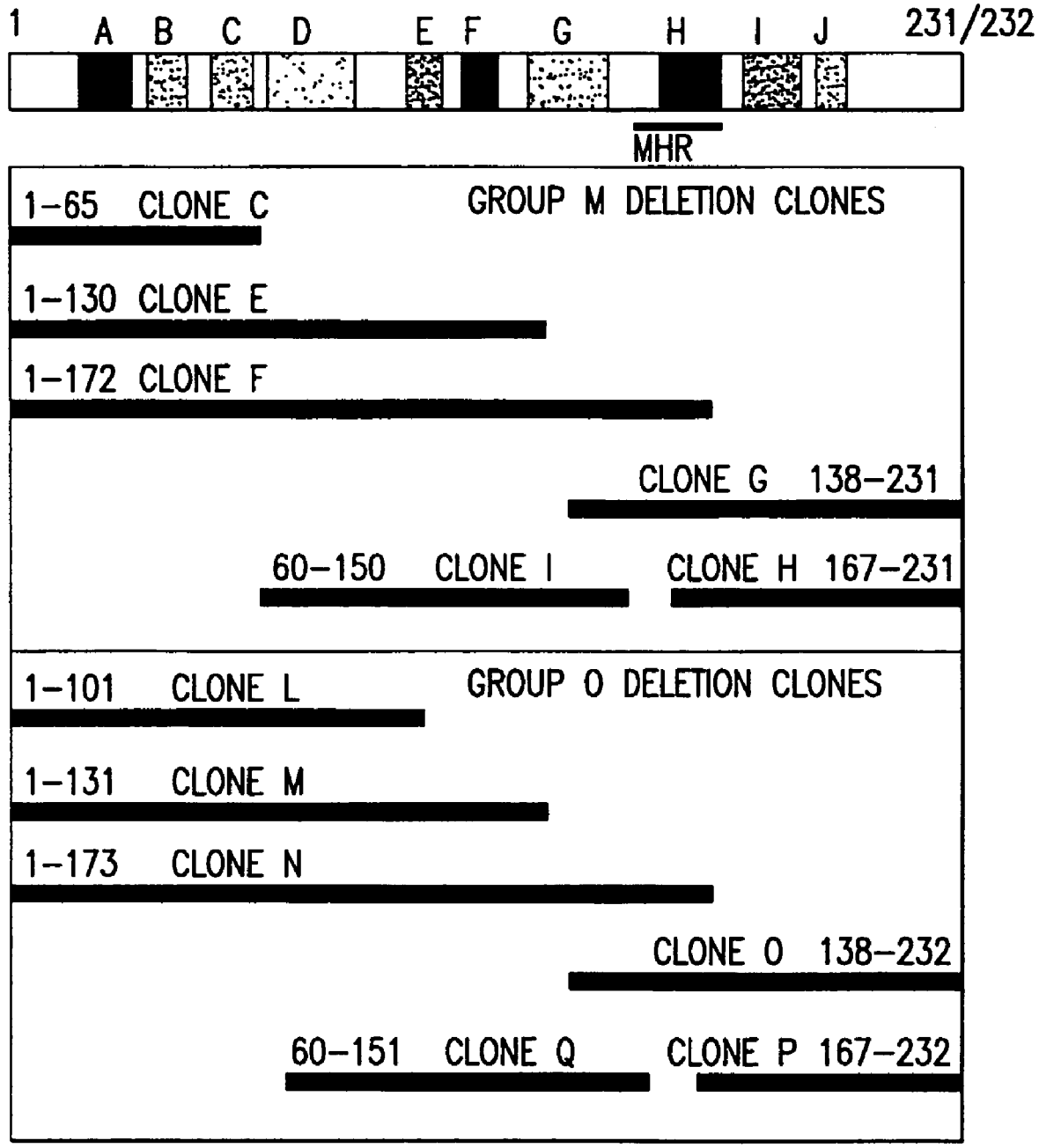
Figure 4B:
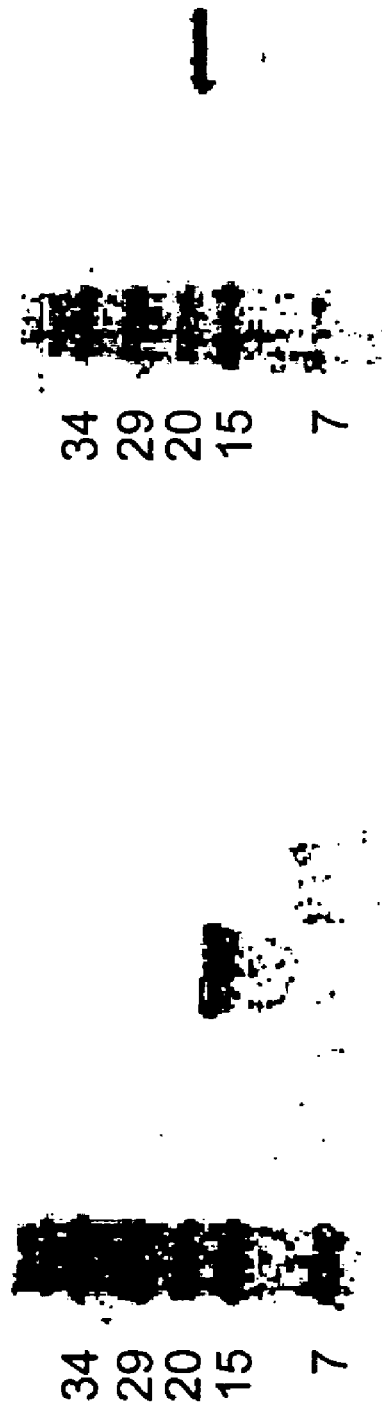
Figure 5:
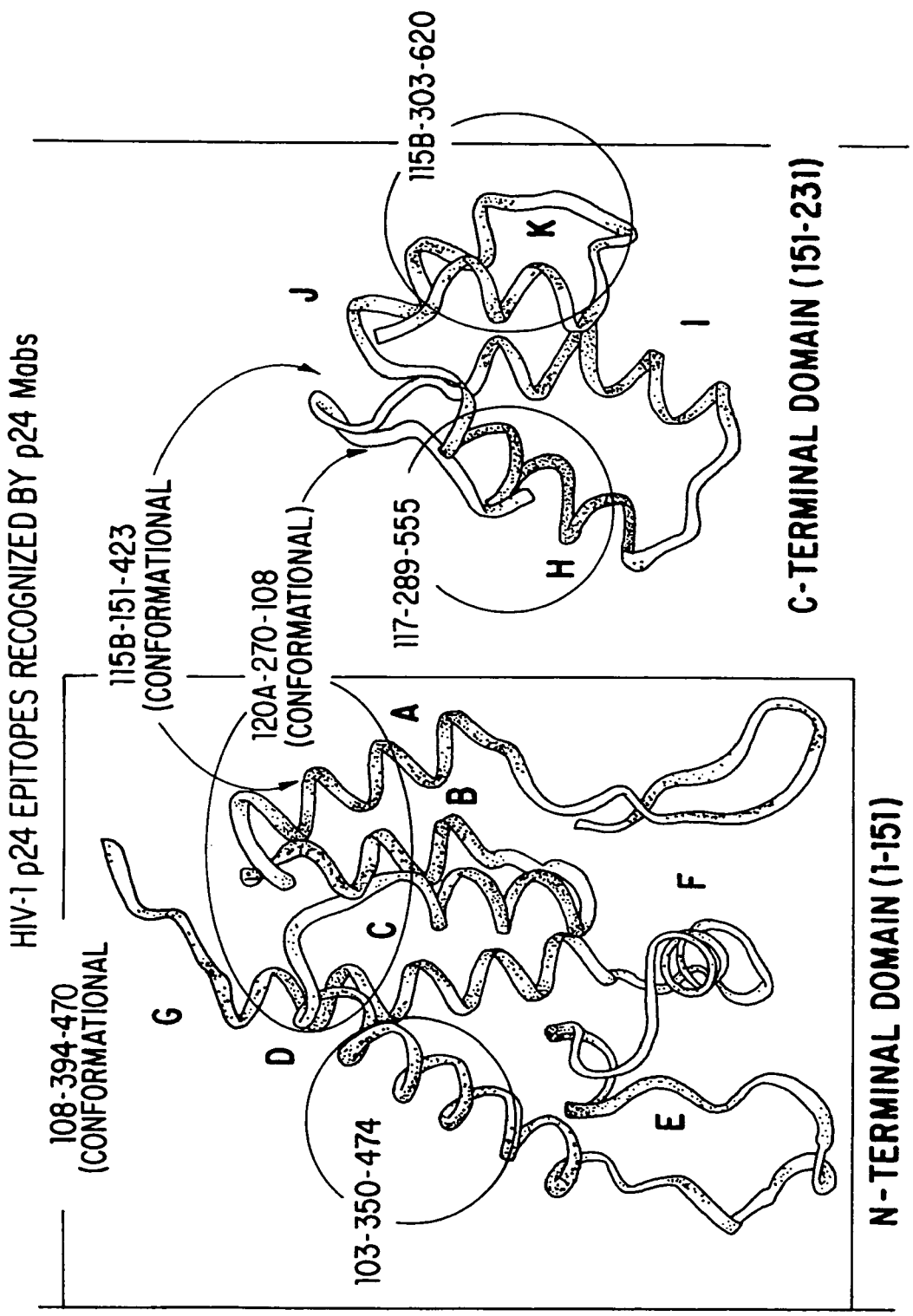

Based on the data from epitope mapping using synthetic peptides and p24 deletion clones and the data from the p24 sandwich compatibility study, an epitope map of the six mAbs on the three dimensional structure of p24 antigen is illustrated in FIG. 5. The structure of the p24 molecule is represented by two domains, the N-terminal domain (amino acids 1-151) and the C-terminal domain (amino acids 151-231). The structure of the intact p24 molecule has not been determined so the exact structural relationship between the two domains is not fully characterized.

The six mAbs mapped to p24 antigen in the following manner (FIG. 5):

Monoclonal antibody 103-350-474 binds a linear epitope located in the helix D region of HIV-1 M and O p24. The epitope is most broadly defined as comprising amino acids 63-89, and is most narrowly estimated as comprising amino acids 63-80 of group M and group O of the p24 antigen.

Monoclonal antibody 117-289-555 binds a linear epitope located in the MHR/helix H region of p24. The epitope is most broadly defined as comprising amino acids 151-172 (M)/152-173 (O), and is most narrowly defined as amino acids 162-172(M)/163-173(O) of p24 antigen.

Monoclonal antibody 115B-303-620 binds a linear epitope located in the helical J-K regions of p24 antigen. The epitope is defined as amino acids 198-217(M)/199-218(O) of the p24 antigen.

Monoclonal antibody 115B-151-423 binds a conformational epitope which is most likely near the junction part of helix A and MHR/helix H regions of p24.

Monoclonal antibody 108-394-470 binds a conformational epitope formed within the N-terminal domain (amino acids 1-151) of p24. The conformational epitope is estimated to be near the junction part of helix D and helix A.

Monoclonal antibody 120A-270-108 binds a conformational epitope which is estimated to be near the junction part of helix D, helix A and MHR/helix H regions of p24.

EXAMPLE 9

Preparation of Monoclonal Antibody Coated Microparticles

Carboxyl-modified latex (CML) microparticles at 1% solid (obtained from Bangs Laboratories, Fishers, Ind.) were activated by carbodiimide EDC [1-ethyl-3-3-dimethylaminopropyl) carbodiimide hydrochloride from Sigma Chemicals, St. Louis, Mo.] at a molar ratio of EDC: carboxyl groups=10:1 in 50 mM MES [2-(N-morpholino)ethane sulfonic acid) buffer pH 6.1 for 5 minutes at RT on a end-over-end rotator (Roto-Torque, Cole Parmer Instruments, Vernon Hills, Ill.) set at high on scale 5. Anti-core Mab was added to EDC pre-activated CML microparticles at a ratio of 200 ug antibody/per ml of 1% solid microparticles for 4 hours at room temperature on an end-over-end rotator. Free reactants were washed away using Abbott diafiltration system (Abbott Laboratories, Abbott Park, Ill.) with a crossflow syringe membrane (0.2 um pore size and 12 $cm^2$ surface area, obtained from Spectrum, Laguna Hills, Calif.). Mab-coated microparticles were overcoated with buffer containing 10 mM PBS and 5% BSA, 0.03% sodium azide for 1 hour at RT on a rotator. Mab-coated CML microparticles were heat-stressed in a 45 C oven incubator for 20 hours and then tested by an Abbott Prism Standalone instrument (Abbott Laboratories, Abbott Park, Ill.).

EXAMPLE 10

Preparation of Acridinium-Labeled Antibody Conjugates

Anti-HIV core Mabs in PBS, pH 7.4 reacted with acridinium-N-hydroxysuciniimide (ACR-NHS) active ester at the molar ratio of Mab:ACR-NHS=1:15 for 10 minutes at RT on an end-over-end rotator (Cole Parmer Instruments, Vernon Hills, Ill.). ACR-labeled-Mab conjugate was separated from free reactants by a G-25 Sephardex column (15 cm×1.5 cm) which was pre-equilibrated in PBS pH 6.3 containing 1% CHAPS. The elution peak of ACR-labeled-Mab was monitored by following absorbance at 280nm using a spectrophotometer (Shimadzu UV-2101PC). The concentration of ACR-labeled-mAb protein=(OD280 nm−0.247×OD370 nm)/1.38. Molar ratios of ACR/mAb=[OD370 nm/(OD280 nm−0.247× OD370 nm)]×15.

EXAMPLE 11

Prism Immunoassay Methods and Preparation

Anti-p24 mAb-microparticles (concentrate stock) were diluted in uParticle diluent (10 mM PBS, pH 6.5 containing 5% calf serum, 7.5% sucrose, 50 mM EDTA, 0.1% Tween 20, and 0.1% proclin). Anti-p24 mAb-ACR conjugates were diluted in conjugate diluent (10 mM PBS, pH 6.3 containing 40 mM EDTA, 5% calf serum, 0.5% Triton, and 0.1% proclin). Two wash buffers were used in the assay. Transfer wash buffer contained 25 mM MES pH 5.7, 150 mM NaCl, 4% Triton X-100, 1% Tween 20, 0.001% PEG, 0.1% proclin, and 0.001% antifoam. Conjugate wash buffer contained 10mM CAPS, pH 9.9, 150 mm NaCl, 5% Triton X-100, 0.1% proclin, and 0.001% antifoam. HIV-1 p24-M, rp24-O, HIV-2 rp26, and HIV-2 viral lysate were diluted in HIV-1/2 negative human plasma. Normal human plasma was also used as a negative control.

Assay Procedure:

Briefly, all reagents were warmed up to room temperature before priming the instrument. Transfer wash buffer, conjugate wash buffer, anti-p24 mAb-ACR conjugate, and activator were connected to a proper reagent line. The reagents were primed two times and any air bubbles trapped in the reagent lines were tapped away. One hundred ul of samples and 50 ul of specimen diluent (25-mM PBS pH 6.5, 1% Triton X-100, 0.4% Tween 20, 20 mM EDTA, and 0.1% proclin) were added into channel A and B reaction wells of sample tray manually. The trays were loaded on the instrument and moved constantly through the channel during the assay steps. When the sample tray moved to the microparticle station, 50 ul of anti-p24 mAb-coated microparticles were added into each reaction well. The rest of the assay steps were performed automatically by the instrument. The channel temperature of the instrument was maintained at 37 C. after 18 minutes incubation at 37 C, the sample tray was moved to the transfer wash station. The mixture of sample and uParticle were flushed onto a glass fiber matrix by transfer buffer and washed 2 times with transfer buffer. Fifty ul of anti-p24 mAb-ACR conjugate were added onto the glass fiber matrix. After 20 minutes incubation, the sample tray was moved to the conjugate wash station. Unbound conjugates were washed away by conjugate wash buffer. After the conjugate wash, the sample tray was moved to the activator station. Fifty ul of activator (mixture of hydrogen peroxide and sodium hydroxide) were applied to the matrix. The chemiluminescence light signal was read by a photomultiplier tube detector.

EXAMPLE 12

Figure 6:
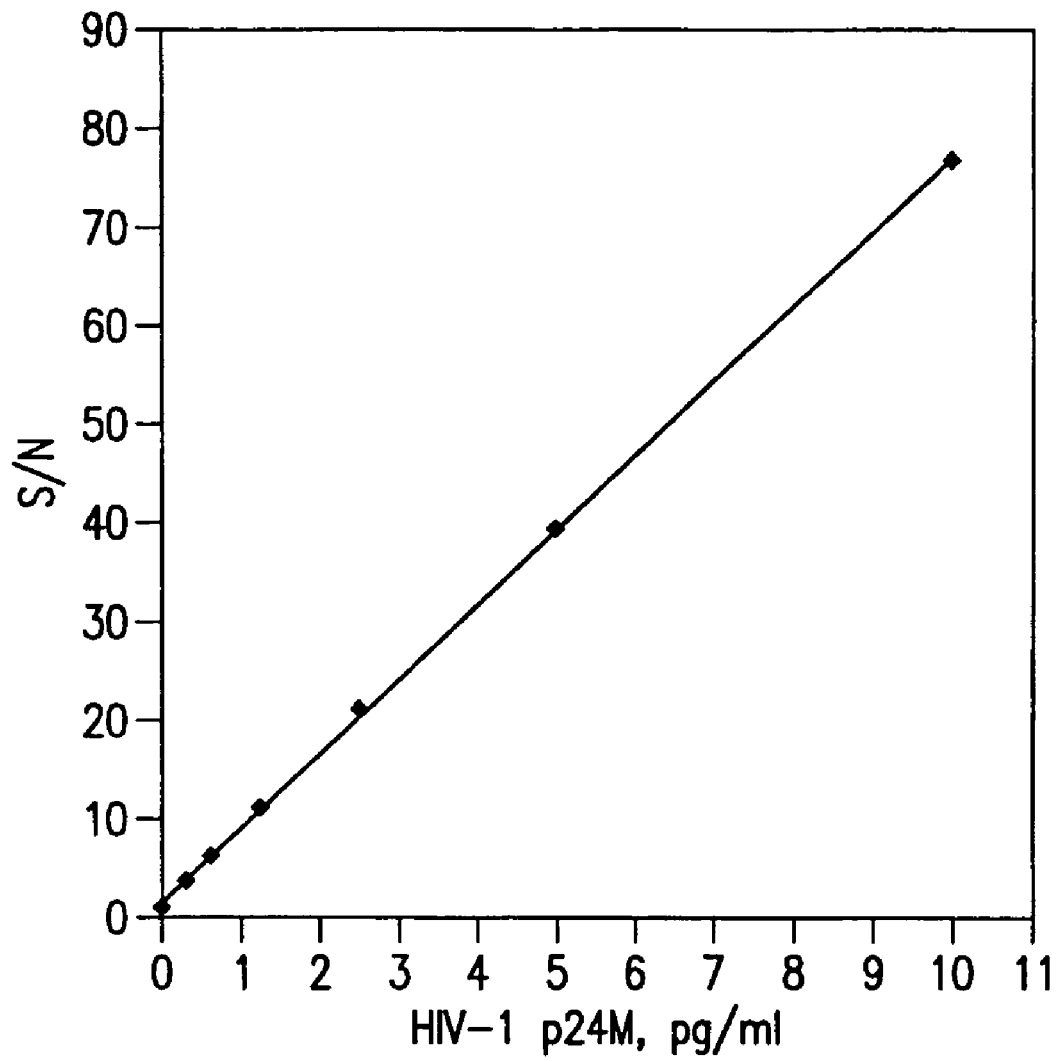
FIG. 6 illustrates HIV-1 group M p24 quantitative sensitivity achived using 120A-270 on a solid phase and 115B-151 in solution phase.
Figure 7:
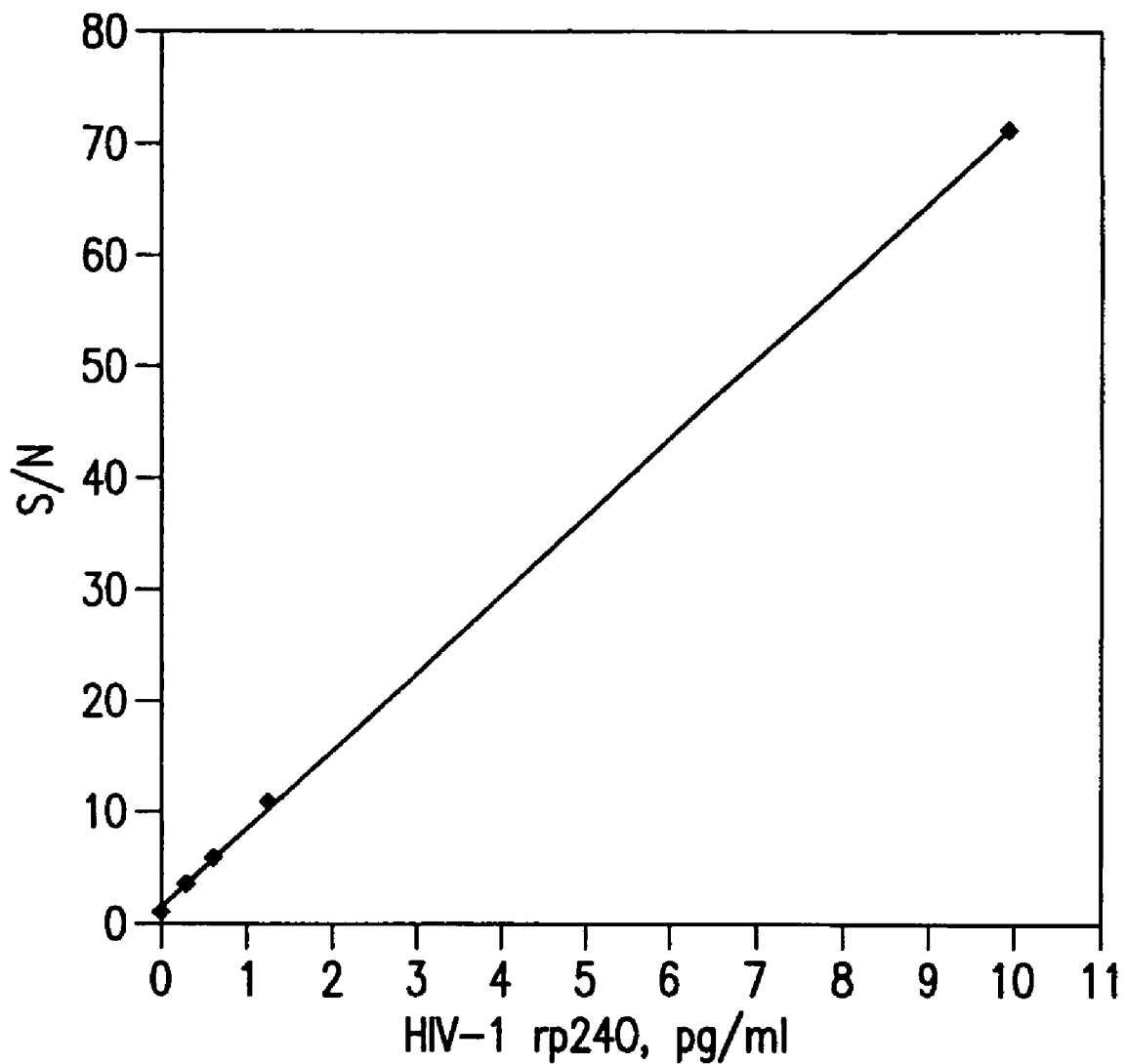
FIG. 7 illustrates HIV-1 group O p24 quantitative sensitivity achieved using 120A-270 on a solid phase and 115B-151 in solution phase.
Figure 8:
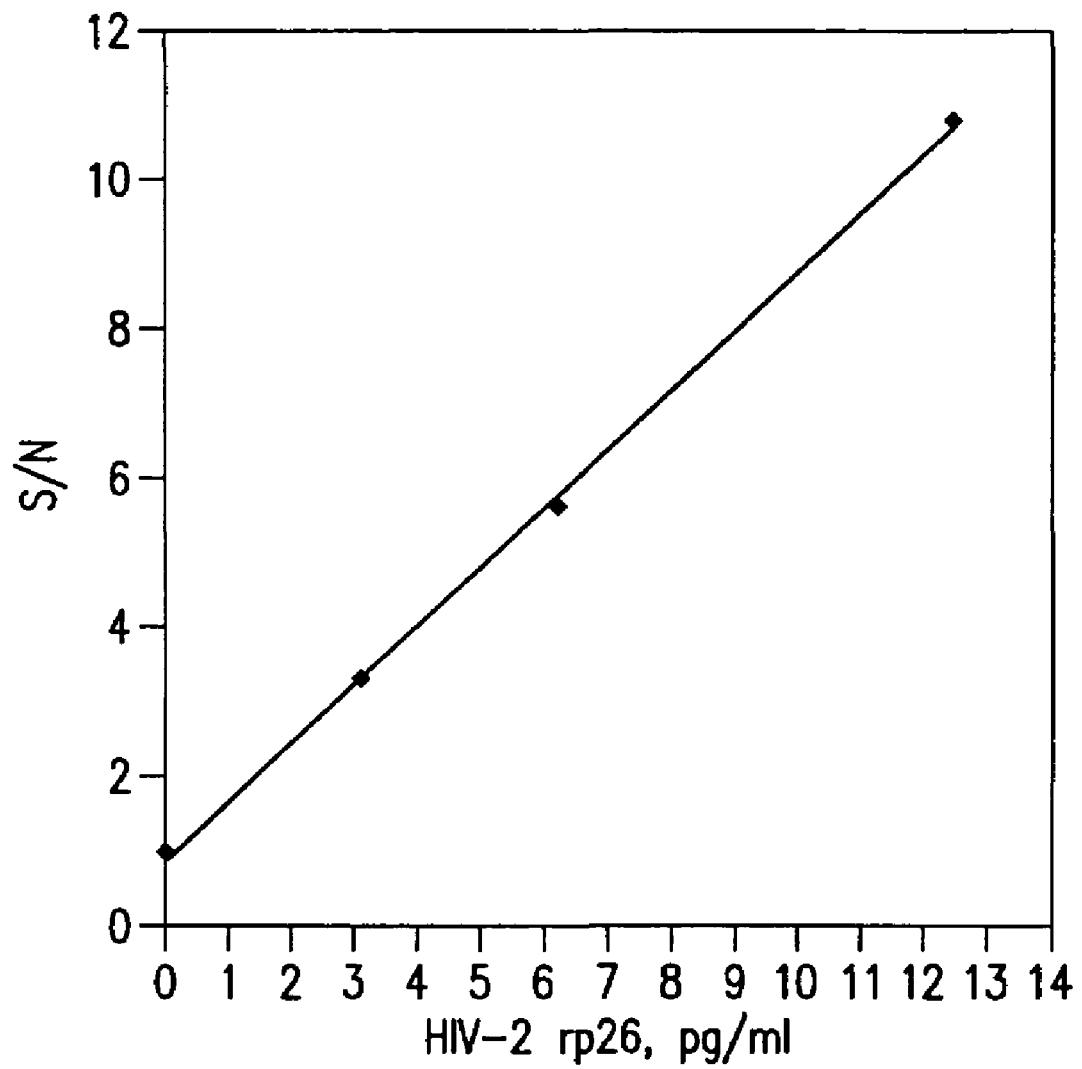
FIG. 8 illustrates HIV-2 p26 quantitative sensitivity achieved using 120A-270 on a solid phase and 115B-151 in solution phase.

Equivalent Detection of HIV Core Proteins (Antigens)Using Two Monoclonal Antibodies Equivalent, quantitative core antigen sensitivity using compatible pairs of high affinity monoclonals was demonstrated in a two-step, chemiluminescent, "sandwich" immunoassay run on an Abbott Prism standalone instrument (Abbott Laboratories, Abbott Park, Ill.). By combining 120A-270-108 coated microparticles (0.066% solid) with 115B-151-423-ACR conjugate at 60 ng/ml, equivalent detection of HIV-1 group M, HIV-1 group O, and HIV-2 core proteins was achieved. The lowest limits of detection for HIV-1 group M p24 was estimated at 0.3 pg/ml(FIG. 6), 0.3 pg/ml for HIV-1 group O rp24 (FIG. 7), and 1.0 pg/ml for HIV-2 rp26 (FIG. 8). Only a small (3.3 folds) differences in quantitative sensitivity was detected between HIV-1 and HIV-2. Equivalent sensitivity across three related but non-indentical core antigens strongly argues that the unusually high Keq of these monoclonal antibodies are directed toward shared epitopes, not cross-reactive epitopes. Affinity of these Mabs against core antigens (HIV-1 M, O, and HIV-2) must be nearly equal because of the near equivalent binding kinetics against all three core antigens. Generally, Keq decreases when Mabs are reacted against cross-reactive epitopes, indicated by markedly lower quantitative sensitivity for the cross-reactive antigen compared to the native (immunogen) antigen. Further, the small differences between quantitation of HIV-1 and HIV-2 core proteins related herein may relate more to the methods and (error around the methods) used to quantitate the proteins for the studies.

The invention claimed is:

1. A monoclonal antibody which binds to a shared epitope of Human Immunodeficiency Virus-1 protein p24 and Human Immunodeficiency Virus-2 protein p26, wherein said monoclonal antibody is 115B-303 produced by the cell line having A.T.C.C. Deposit No. PTA-2810.

2. A hybridoma cell line which secretes a monoclonal antibody which binds to a shared epitope of Human Immunodeficiency Virus-1 protein p24 and Human Immunodeficiency Virus-2 protein p26, wherein said cell line is A.T.C.C. Deposit No. PTA-2810.

3. A kit for determining the presence of one or more antigens selected from the group consisting of HIV-1 antigen and HIV-2 antigen in a test sample comprising: (a) at least one monoclonal antibody which binds to a shared epitope of Human Immunodeficiency Virus-1 protein p24 and Human Immunodeficiency Virus-2 protein p26, wherein said at least one monoclonal antibody is 115B-303 produced by the cell line having A.T.C.C. Deposit No. PTA-2810; and (b) a conjugate comprising an antibody attached to a signal generating compound capable of generating a detectable signal.

4. A diagnostic reagent comprising at least one monoclonal antibody wherein said at least one monoclonal antibody is 115B-303 produced by the cell line having A.T.C.C. Deposit No. PTA-2810.

* * * * *